(12) United States Patent
Smith

(10) Patent No.: US 10,451,480 B2
(45) Date of Patent: Oct. 22, 2019

(54) SYSTEMS AND METHODS FOR CHEMICAL ANALYSIS USING FABRY-PEROT TUNABLE FILTER-ATTENUATED TOTAL REFLECTANCE (FPTF-ATR) SPECTROMETER

(71) Applicant: Big Sur Scientific, LLC, Aptos, CA (US)

(72) Inventor: Brian Charles Smith, Aptos, CA (US)

(73) Assignee: Big Sur Scientific, LLC, Aptos, CA (US)

( * ) Notice: Subject to any disclaimer, the term of this patent is extended or adjusted under 35 U.S.C. 154(b) by 0 days.

(21) Appl. No.: 16/372,725

(22) Filed: Apr. 2, 2019

(65) Prior Publication Data

US 2019/0226912 A1    Jul. 25, 2019

Related U.S. Application Data

(63) Continuation of application No. PCT/US2017/057771, filed on Oct. 22, 2017.
(Continued)

(51) Int. Cl.
*G01J 3/26* (2006.01)
*G01N 21/552* (2014.01)
(Continued)

(52) U.S. Cl.
CPC .............. *G01J 3/26* (2013.01); *G01J 3/0208* (2013.01); *G01J 3/0286* (2013.01);
(Continued)

(58) Field of Classification Search
CPC .................................. G01N 21/552; G01J 3/26
See application file for complete search history.

(56) References Cited

U.S. PATENT DOCUMENTS 3,487,223 A    12/1969   St. John
4,602,869 A *   7/1986   Harrick ................ G01N 21/552
                                                          356/244
(Continued)

FOREIGN PATENT DOCUMENTS

CN    201429564 Y    3/2010
CN    101592598 B    9/2010
(Continued)

OTHER PUBLICATIONS

Neumanna, Norbert, et al., "Tunable infrared detector with integrated micromachined Fabry-Perot filter," Journal of Micro/Nanolithography, MEMS, and MOEMS 7(2), 021004, Apr. 1, 2008. https://doi.org/10.1117/1.2909206.

*Primary Examiner* — Shawn Decenzo
(74) *Attorney, Agent, or Firm* — American Patent Agency PC; Daniar Hussain

(57) ABSTRACT

Disclosed is a combination of a Fabry-Perot Tunable Filter (FPTF) wavelength selector, an internal reflection element (IRE) capable of measuring Attenuated Total Reflectance (ATR) spectra, and a pressure application element for applying pressure to samples, if needed. The resultant portable and compact device is called an FPTF-ATR spectrometer. The device measures data that can be used to identify chemical species in samples, predict properties of samples, and quantify amounts of chemical species in samples. Also disclosed are methods for using the FPTF-ATR for analyzing samples, especially analyzing compounds containing *cannabis*, hops, and other chemical species where portable chemical analysis is important.

13 Claims, 15 Drawing Sheets

Related U.S. Application Data

(60) Provisional application No. 62/412,790, filed on Oct. 25, 2016.

(51) Int. Cl.
  G01J 3/02 (2006.01)
  G01N 33/94 (2006.01)
  G01J 3/12 (2006.01)

(52) U.S. Cl.
  CPC ......... *G01N 21/552* (2013.01); *G01N 33/948* (2013.01); *G01J 2003/1247* (2013.01); *G01N 2201/0221* (2013.01)

(56) References Cited

U.S. PATENT DOCUMENTS

| | | |
|---|---|---|
| 5,437,840 A | 8/1995 | King et al. |
| 5,538,850 A | 7/1996 | King et al. |
| 6,419,559 B1 | 7/2002 | Gurusamy |
| 8,581,194 B2 | 11/2013 | Mikkelsen et al. |
| 2003/0052569 A1* | 3/2003 | Dhuler .................. H02N 1/006 310/309 |
| 2005/0083533 A1* | 4/2005 | Atia ......................... G01J 3/10 356/454 |
| 2007/0182959 A1* | 8/2007 | Maier ................... G01J 3/2803 356/301 |
| 2008/0257872 A1* | 10/2008 | Muys ..................... B23K 26/06 216/121.67 |
| 2013/0275052 A1 | 10/2013 | Loder et al. |
| 2016/0016138 A1 | 1/2016 | Hung et al. |
| 2016/0061807 A1* | 3/2016 | Ravishankar ........ G01N 33/487 506/6 |
| 2016/0223466 A1* | 8/2016 | Mano ................... G02B 6/1225 |
| 2017/0082846 A1* | 3/2017 | Rowlette .............. G02B 21/361 |
| 2018/0306726 A1* | 10/2018 | Mannhardt ........ G01N 21/8507 |

FOREIGN PATENT DOCUMENTS

| | | |
|---|---|---|
| WO | WO2016168090 A1 | 10/2016 |
| WO | WO2018080938 A1 | 5/2018 |

* cited by examiner

SYSTEMS AND METHODS FOR CHEMICAL ANALYSIS USING FABRY-PEROT TUNABLE FILTER-ATTENUATED TOTAL REFLECTANCE (FPTF-ATR) SPECTROMETER

REFERENCE TO RELATED APPLICATIONS

This application is a continuation of and claims priority from PCT Application Ser. No. PCT/US17/57771, filed on 22 Oct. 2017, and entitled "Systems and Methods for Chemical Analysis Using Fabry-Perot Tunable Filter-Attenuated Total Reflectance (FPTF-ATR) Spectrometer," which itself claims the benefit of priority to provisional application U.S. Ser. No. 62/412,790, filed on 25 Oct. 2016, and entitled "Systems and Methods for Sample Analysis," the entire disclosures of both of which are hereby incorporated by reference in their entireties herein.

FIELD OF THE INVENTION

Embodiments of the present invention relate to the field of spectroscopy, and pertain particularly to spectrometer design, as well as methods of using such spectrometers for chemical analysis of various samples.

BACKGROUND OF THE INVENTION

Spectroscopy is the study of the interaction of electromagnetic (EM) radiation, or "light," with matter [1]. Instruments called spectrometers are used in spectroscopy to measure what are called spectra [1]. Spectra are typically a plot of light intensity on the y-axis versus some property of light on the x-axis, as measured by a spectrometer. The y-axis units may include, but are not limited to, absorbance, transmittance, percent transmittance, reflectance, logarithm of reflectance, percent reflectance, and arbitrary intensity. X-axis units may include, but are not limited to, wavelength, wavenumber, and frequency. Spectrometers can be used to measure spectra of samples. Spectra are useful because they contain information about samples including sample properties, the identity and the amount of chemical species present in a sample [2,3]. Chemical species include, but are not limited to, atoms, molecules, elements, ions, anions, cations, polyatomic cations, polyatomic anions, and polymeric molecules. Spectra may be used to predict any property of a sample including, examples including but not limited to viscosity, octane number, and pH [3].

The types of samples that spectrometers can analyze can be divided up into the three phases of matter: solids, liquids, and gases. For all three phases of matter, there is a need to identify and quantify the chemical species in samples. There exist general use spectrometers capable of performing this type of work, but they are often expensive, difficult to use, and bulky. For example, to calibrate a modern laboratory Fourier Transform Infrared Spectrometer (FTIS) to determine potency in marijuana buds took over a year of time for a Ph.D. scientist. It would be advantageous if such analyzers were made smaller and lightweight so they could be used outside the lab, easier to use so that many more people could use them, and pre-calibrated so that a highly educated scientist is not needed to make them functional.

Furthermore, some spectrometers of interest are only capable of working on gas samples. Given that much of the matter of analytical interest is in solid or liquid form, the advantages of such spectrometers cannot be brought to bear on these samples.

Therefore, in view of the aforementioned difficulties, there is an unsolved need for methods and systems for a compact and portable spectrometer. In addition, it would be an advancement in the state of the art to incorporate methods and systems for analysis of chemical properties of gases, solids, and liquids into a simple spectrometer. Finally, it would be a further advancement in the state of the art in one particular scenario to provide a spectrometer for the analysis of *cannabis*-based fluid- and solid-based products in a compact form factor.

It is against this background that various embodiments of the present invention were developed.

BRIEF SUMMARY OF THE INVENTION

In one aspect, the present invention solves these problems by combining an internal reflection element (IRE) with one or more sampling surfaces capable of measuring attenuated total reflectance (ATR) spectra with a Fabry-Perot Tunable Filter (FPTF), to comprise a Fabry-Perot Tunable Filter-Attenuated Total Reflectance (FPTF-ATR) spectrometer. This enables the novel spectrometer to take spectra of any solid or liquid that can be brought into contact with one or more of its sampling surfaces. Subsequent spectral analysis allows the identity and amount of chemical species and other properties of these samples to be determined. For example, using a pre-calibrated FPTF spectrometer equipped with an IRE, the potency of marijuana buds can be determined outside the lab by non-technical personnel with no sample preparation in about two minutes.

Accordingly, one embodiment of the present invention is a device comprising a combination of a Fabry-Perot Tunable Filter (FPTF) wavelength selector, an internal reflection element (IRE) capable of measuring Attenuated Total Reflectance (ATR) spectra, and a pressure application element for applying pressure to samples, if needed. The device measures data that can be used to identify chemical species in samples, predict properties of samples, and quantify the amounts of chemical species in samples.

More specifically, in one aspect, one embodiment of the present invention is a chemical analysis device for analyzing a sample, comprising a source of electromagnetic radiation optically coupled to a first set of transfer optics; an internal reflection element capable of forming an evanescent wave at one or more surfaces, said surface(s) capable of being exposed to a sample thus being sampling surfaces, the internal reflection element optically coupled to said first set of transfer optics; a second set of transfer optics optically coupled to said internal reflection element; a Fabry-Perot tunable filter wavelength selector optically coupled to said second set of transfer optics, said Fabry-Perot tunable filter comprising at least one mobile reflective surface for adjusting bandpass wavelengths; a detector element optically coupled to said Fabry-Perot tunable filter that turns electromagnetic radiation into a signal; and a communication element to send the signal to a control, display, and data analysis device.

Some embodiments of the present invention further comprise a reflective surface moving element for moving the mobile reflective surface of the Fabry-Perot tunable filter. In some embodiments of the present invention, the reflective surface moving element is a voltage-actuated electrostatic spring. In some embodiments of the present invention, the source of electromagnetic radiation is pulsed. In some embodiments of the present invention, the first set of transfer optics comprises a mirror and a Zinc Selenide (ZnSe) lens, and the second set of transfer optics comprises a mirror and a ZnSe lens. In some embodiments of the present invention, the first set of transfer optics comprises a ZnSe lens, and the second set of transfer optics comprises a ZnSe lens. In some embodiments of the present invention, the first set of transfer optics comprises a parabolic mirror. In some embodiments of the present invention, the internal reflection element material is selected from the group consisting of zinc selenide, silicon, diamond, germanium, and thallium bromoiodide (KRS-5). In some embodiments of the present invention, the detector element material is selected from the group consisting of deuterated triglycine sulfate, triglycine sulfate. lithium tantalate, mercury cadmium telluride, lead sulfide, silicon, germanium, indium antimonide, indium arsenic antimonide, and indium gallium arsenide. In some embodiments of the present invention, the sample is selected from the group consisting of a liquid, a solid, and a solid-liquid mixture. In some embodiments of the present invention, the sample is selected from the group consisting of a *cannabis* containing liquid, a *cannabis* containing solid, and a *cannabis* containing solid-liquid mixture.

In another aspect, another embodiment of the present invention is a chemical analysis device, comprising a source of electromagnetic radiation optically coupled to a first set of transfer optics; an internal reflection element (IRE) capable of forming an evanescent wave at one or more surfaces, said surface(s) capable of being exposed to a sample thus being sampling surfaces; a pressure application element for applying pressure to the sampling surface(s) or a sample resting upon the sampling surface(s); a second set of transfer optics optically coupled to said internal reflection element; a Fabry-Perot tunable filter wavelength selector optically coupled to said second set of transfer optics, said Fabry-Perot tunable filter comprising at least one mobile reflective surface for adjusting bandpass wavelengths; a detector element optically coupled to said Fabry-Perot tunable filter that turns electromagnetic radiation that passes through the internal reflection element and interacts with the sample into a signal; and a communication element to send the signal to a control, display, and data analysis device.

In some embodiments of the present invention, the pressure application element is a clamp. Some embodiments of the present invention further comprise a pressure measurement element for measuring and controlling an amount of pressure applied by the pressure application element to the sampling surface. In some embodiments of the present invention, the pressure application element comprises a slip-clutch element, wherein an amount of pressure applied is limited by the slip-clutch element. In some embodiments of the present invention, the source of electromagnetic radiation is pulsed. In some embodiments of the present invention, the first set of transfer optics comprises a mirror and a ZnSe lens, and the second set of transfer optics comprises a mirror and a ZnSe lens. In some embodiments of the present invention, the first set of transfer optics comprises a ZnSe lens, and the second set of transfer optics comprises a ZnSe lens. In some embodiments of the present invention, the first set of transfer optics comprises a parabolic mirror. In some embodiments of the present invention, the internal reflection element is made of a material selected from the group consisting of zinc selenide, silicon, diamond, germanium, and KRS-5. In some embodiments of the present invention, the detector element is made of a material selected from the group consisting of deuterated triglycine sulfate, triglycine sulfate. lithium tantalate, mercury cadmium telluride, lead sulfide, silicon, germanium, indium antimonide, indium arsenic antimonide, and indium gallium arsenide. In some embodiments of the present invention, the sample is selected from the group consisting of a liquid, a solid, and a solid-liquid mixture. In some embodiments of the present invention, the sample is selected from the group consisting of a *cannabis* containing liquid, a *cannabis* containing solid, and a *cannabis* containing solid-liquid mixture.

In yet another aspect, yet another embodiment of the present invention is a chemical analysis method, comprising the steps of taking the electromagnetic radiation from an electromagnetic radiation source and coupling it to a first set of transfer optics; optically coupling the first set of transfer optics to an internal reflection element, wherein an evanescent wave is formed on one or more of its sampling surface(s); placing a sample on one or more of the sampling surface(s); applying pressure to the sample if needed to insure good contact with the evanescent wave, allowing the sample to interact with the evanescent wave; optically coupling the EM radiation with a second set of transfer optics; optically coupling the second set of transfer optics with a Fabry-Perot tunable filter; using said Fabry-Perot tunable filter to determine an amount of light absorbed by the sample at a plurality of wavelengths comprising the sample's spectrum; and analyzing the spectrum to determine chemical species present in the sample, quantify the chemical species present in the sample, classify the sample, or determine one or more properties of the sample.

In some embodiments of the present invention, the sample is selected from the group consisting of a liquid, a solid, and a solid-liquid mixture. In some embodiments of the present invention, the sample is selected from the group consisting of a *cannabis* containing liquid, a *cannabis* containing solid, and a *cannabis* containing solid-liquid mixture. In some embodiments of the present invention, spectral analysis involves use of spectral peak heights and areas. In some embodiments of the present invention, the spectral analysis involves use of a multivariate chemometric algorithm including but not limited to principal component analysis, principal component regression, and partial least squares.

Yet other aspects of the present invention include the methods and processes comprising the steps described herein, and also include the processes and modes of operation of the systems and devices described herein. Other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings. For purposes of clarity, not every component is labeled in every drawing. The drawings are not drawn to scale, with emphasis instead being placed on illustrating various aspects of the techniques and devices described herein.

DETAILED DESCRIPTION OF THE INVENTION

Illustrative Definitions

Figure 1:
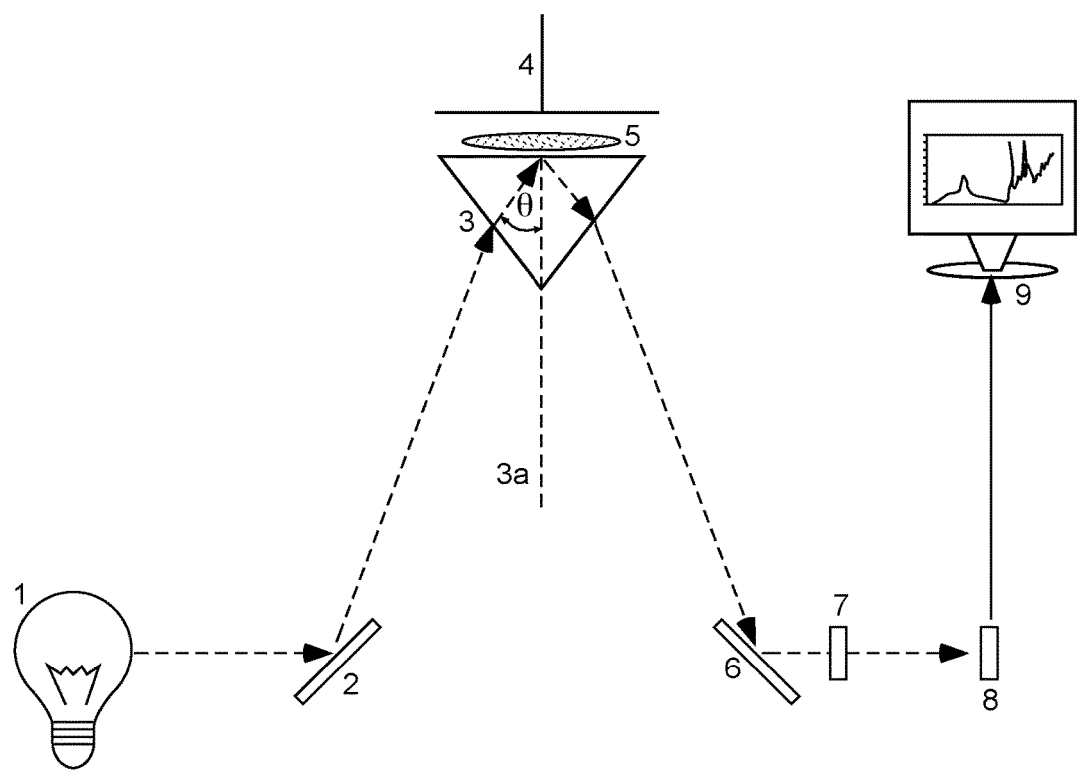
FIG. 1 shows a schematic of a spectrometer device comprising a Fabry-Perot Tunable Filter-Attenuated Total Reflectance (FPTF-ATR) spectrometer ("device"), according to one embodiment of the present invention.

In the following description, for purposes of explanation, numerous specific details are set forth in order to provide a thorough understanding of the invention. It will be apparent, however, to one skilled in the art that the invention can be practiced without these specific details. In other instances, structures, devices, activities, methods, and processes are shown using schematics, use cases, and/or diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Some illustrative definitions are provided to assist in understanding the present invention, but these definitions are not to be read as restricting the scope of the present invention. The terms may be used in the form of nouns, verbs, or adjectives, within the scope of the definition.

"Spectroscopy" is the study of the interaction of electromagnetic (EM) radiation ("light") with matter through the analysis of spectra [1].

"Spectra" are typically a plot of light intensity, as measured by a spectrometer, on the y-axis, versus some property of light, such as wavelength, on the x-axis.

A "spectrometer" is an instrument that can be used to measure spectra of samples.

A "Fabry-Perot Interferometer (FPI)" is defined as an optical cavity with two immobile reflective surfaces. The FPI then acts as a static filter, only allowing a fixed bandwidth of wavelengths to pass through. Therefore, a FPI is not scannable, meaning the bandpass wavelengths cannot be changed. An FPI is also sometimes known as a "Fabry-Perot filter."

A "Fabry-Perot Tunable Filter (FPTF)," in contrast, has a "mobile" reflective surface allowing the FPTF to be scanned across a spectrum of wavelengths, allowing a non-fixed bandwidth of radiation to pass. This means FPTF is scannable, and its bandpass wavelengths can be changed. This allows the measurement of absorbance values at multiple wavelengths, comprising a spectrum, rather than at a set of fixed wavelengths as in a FPI. The term "Fabry-Perot Tunable Filter" is used to emphasize its scanning abilities.

A "reflective surface" is a mirror, or the like, that reflects EM radiation.

A "mobile reflective surface" is a movable mirror, or the like, that can be moved by a mechanical element, by an electrical element, or the like.

A "reflective surface moving element" is used to move the mobile reflective surface. In some embodiments, the mobile reflective surface has a spring attached to the sides of its back to allow the passage of EM radiation. In one embodiment, a voltage is swept which electrostatically moves the mobile reflective surface, which gives it the ability to scan multiple bandpass wavelength ranges. Other examples of ways to move the mobile reflective surface include, but are not limited to, direct drive motors, piezoelectric motors, and mechanical devices for effecting the motion.

An "Internal Reflection Element (IRE)" is comprised of a high refractive index material, in this context meaning a refractive index greater than that of any sample that may be brought into contact with the IRE. A beam of EM radiation impinging upon a surface of an IRE can refract into the body of the IRE. If upon approaching a surface of the IRE, said beam has an angle of incidence ($\theta$ in FIG. 1) greater than the critical angle $\theta_c$ of the IRE material, it will be totally internally reflected, and the EM beam will stay within the IRE. The critical angle $\theta_c$ of an IRE is defined as [1]

$$\theta_c = \sin^{-1}(n_s/n_c) \quad (1)$$

where
$\theta_c$=critical angle of IRE material,
$n_s$=refractive index of the sample, and
$n_c$=refractive index of the IRE.

At the point of total internal reflectance, the incoming and outgoing beams may constructively interfere, giving EM amplitude at this point greater than that of the incoming or outgoing beams and forming what is called an evanescent wave. Some of the evanescent wave may stick up above the surface of the IRE. Samples may be brought into contact with this evanescent wave, absorb some of the EM radiation, and subsequent spectral analysis of the EM beam will yield the sample's spectrum. This technique of measuring a sample's spectrum with an evanescent wave is called Attenuated Total Reflectance (ATR) spectroscopy. Any surface of an IRE where an evanescent wave forms can be used as a "sampling surface." In one embodiment of the present invention, a top surface of the IRE is used as a sampling surface.

The depth of penetration, DP, is a measure of how far the evanescent wave penetrates into a sample and is given by the following equation [1]

$$DP = 1/[2\pi W n_c (\sin^2\theta - n^2_{sc})^{1/2}] \quad (2)$$

where
DP=depth of penetration,
W=wavenumber,
$N_c$=refractive index of IRE,
$\theta$=angle of incidence, and
$n_{sc}$=refractive index of sample/refractive index of IRE.

For a ZnSe IRE, a 45° angle of incidence, at 1000 cm$^{-1}$ and an organic sample with a refractive index of approximately 1.4, the DP is about 1 micron. This will of course change depending upon the angle of incidence, IRE, sample, and wavenumber.

An "Attenuated Total Reflectance (ATR) spectrometer" is a spectrometer that uses the technique of using an IRE to couple an evanescent wave to a sample for spectroscopic analysis.

A "Fabry-Perot Tunable Filter-Attenuated Total Reflectance (FPTF-ATR) spectrometer" is a novel spectrometer device that comprises a Fabry-Perot Tunable Filter optically coupled to an IRE to measure the ATR spectra of samples. This novel FPTF-ATR spectrometer is sometimes more simply referred to as a "device" in this specification.

A "clamp" or "pressure application element" is an element for providing pressure to a sampling surface. The inventor's work has shown that the clamp is always required for the analysis of solids, and may be required for the analysis of some viscous liquids, which teaches against conventional wisdom. Examples of clamps, or pressure application devices, include, but are not limited to, mechanical elements, such as levers, springs, weights, screws, screw type clamps, screw type clamps with a "slip-clutch" mechanism, and C-clamps. A method for insuring that a reproducible pressure is applied to samples is needed for accurate peak heights for quantitative analysis, for which a pressure measuring element is used. The pressure measuring element may be a mechanical gauge, transducer, or a slip-clutch mechanism that will stop applying pressure at a pre-set pressure value. Devices for communicating the pressure reading and making it known to a user may be used. Such devices may include an electronic display on a clamp, or a separate device for displaying the pressure. The pressure reading may be communicated by wire or wirelessly from the pressure measuring element.

Furthermore, a FPI-ATR spectrometer equipped with a clamp can be used to take spectra of liquids, even when the clamp is not used. Therefore, the presence of the clamp expands the range of samples that can be analyzed from just liquids, to solids and liquids (of all viscosities).

Overview of FPTF-ATR Spectrometer

One embodiment of the present invention is a novel type of spectrometer device (or simply, "device") and methods of using it for the analysis of samples. A schematic diagram of the device is shown in FIG. 1. The device uses electromagnetic (EM) radiation, or light, to interrogate samples. The source of the EM radiation is an electromagnetic or light source 1 shown in FIG. 1. The source may emit electromagnetic radiation of any wavelength, including, but not limited to, x-ray, ultraviolet, visible, near-infrared, mid-infrared, far infrared, microwave, and radio-wave wavelengths. The source may be a laser emitting a single or narrow band of wavelengths, or an emitter source giving off a range of wavelengths.

The source may include a means for mechanically chopping the EM radiation beam to discriminate against background EM radiation and improve signal-to-noise ratio. Alternatively, a means for pulsing the source on and off may be used for this purpose. In one embodiment, the source emits mid-infrared light and is electrically pulsed, and may be comprised of a resistively heated element, such element comprising either a metallic or ceramic element. Element 2 in FIG. 1 denotes one or more optical elements comprising a first set of transfer optics. The optical element or elements of the first set transfer optics include, but are not limited to, lenses and mirrors of any shape, size, materials, and properties. In one embodiment, the first set of transfer optics comprises a parabolic aluminum mirror and a Zinc Selenide (ZnSe) lens. The purpose of the first set of transfer optics is to direct the EM radiation towards the surface of an internal reflection element (IRE) 3 in FIG. 1.

The IRE is comprised of a high refractive index material. In this context, high refractive index means the refractive index of the IRE is greater than that of any sample material placed in contact with the IRE's surface(s). Many different materials of high refractive index may be used to comprise an IRE. Example materials include, but are not limited to, diamond, germanium, silicon, zinc selenide, and thallium bromoiodide (KRS-5). The IRE may comprise, but not be limited to, a single material, be a crystal, be a laminate, be comprised of multiple appropriate materials, or be a diamond, diamond laminate, or monolithic diamond in construction. The IRE may be of any shape or size. Shape examples include, but are not limited to, prisms, cylinders, rods, cones, rectangles, parallelepipeds, triangles, pyramids, squares, ellipses, spheres, hemispheres, troughs, and cubes.

EM radiation impinging upon the surface of an IRE can enter the IRE and refract towards a surface of the crystal [4]. When the EM radiation reaches a surface of the IRE, if the beam's angle of incidence, $\theta$ in FIG. 1, is greater than what is known as the critical angle $\theta_c$ of the IRE crystal material, then the EM beam will undergo total internal reflectance from an internal surface of the crystal [4] as indicated in FIG. 1. The angle of incidence $\theta$ is defined as the angle between the surface normal (3a in FIG. 1) of the IRE and the incoming beam of EM radiation inside the IRE as it approaches a sampling surface as seen in FIG. 1. If $\theta$ is greater than the critical angle of the IRE material $\theta_c$, an evanescent wave will form at the point(s) of internal reflectance, and as a result EM radiation amplitude will penetrate above the surface of the IRE [4]. Any point on any surface of the IRE where the evanescent wave forms can be used as a sampling point or sampling surface.

The sample 5 is placed in contact with part of a sampling surface, a sampling surface, or sampling surfaces of the IRE where an evanescent wave has formed, allowing the sample to interact with the evanescent wave. This surface part, surface, or surfaces will henceforth be called the "sampling surface(s)." The sample may be any solid, fluid, gas, liquid, or solid-liquid mixture. Examples of solids that may be analyzed comprise, but are not limited to, polymers, powders, sheets, blocks, fibers, particles, crystals, crystalline, and amorphous materials. Example of fluids that can be analyzed include, but are not limited to, oils, solvents, colloids, and emulsions. Examples of solid-liquid mixtures include, but are not limited to, gels, pastes, foams, and aerosols.

The sample's spectrum is comprised of light that has been absorbed, reflected, transmitted, scattered, refracted, and diffracted by the sample. The amount of EM radiation leaving the sample at different wavelengths and thus the sample's spectrum may subsequently be detected. The technique of using an IRE to couple an evanescent wave to a sample is known as Attenuated Total Reflectance (ATR) [4] or Attenuated Total Reflectance spectroscopy.

A means for holding and positioning samples may be used. The means for holding samples may comprise, but is not limited to, clamps, holders, troughs, or cells. For softer samples, such as liquids, solutions, fluids, gels, pastes, colloids, emulsions, oils, syrups, and semi-solids, the sample material can be placed directly on a top surface of the IRE and interact with the evanescent wave directly. However, for some particularly thick, viscous, or sticky fluids, things having for example the consistency of saltwater taffy, pressure may be needed to be applied to the sample to insure good coupling of the evanescent wave to the sample, and hence insure measurement of a good spectrum. This teaches against the literature [1]. For harder samples, including but not limited to powders, polymers, and solids, pressure can be applied to insure good contact with the evanescent wave via a pressure application element. The pressure application element is illustrated at 4 in FIG. 1. Pressure may be applied to the sample using any mechanism. Examples of pressure application elements include, but are not limited to, mechanical elements such as levers, springs, weights, and screws. The pressure application element may comprise, but is not limited to, a clamp. The clamp may contain a pressing surface that makes contact with the sample and be of any shape or form, including but not limited to, a flat surface, a curved surface, or a slanted surface, which typically, but is not necessarily limited to, being a flat surface as illustrated at 4 in FIG. 1. The clamp may be actuated manually, or via an electrical means using a motor or similar element.

For quantitative analysis, it is important to control and reproduce the amount of pressure applied to samples [1] to obtain reproducible peak heights. The pressure application element may comprise a mechanism for measuring pressure, including, but not limited to, a pressure transducer. It may be useful to display the pressure being applied to samples. Pressure reading output devices may include, but are not limited to, mechanical gauges, analog or digital electronic displays, including but not limited to, computer monitors, tablet computers, and mobile phone screens. The pressure display may be an integral part of the pressure clamp, such as being a gauge from which the pressure is read visually, or it may communicate the pressure measurement to an outside device via a wire or wirelessly. Instead of a pressure measuring element, the clamp may have a "slip clutch" mechanism that slips and stops applying force to the sample after a specific pressure is exceeded. Alternatively, a mechanical means of recording pressure, including, but not limited to, a gauge or dial may be used.

After the EM beam has interacted with the sample, the EM beam leaves the IRE as seen in FIG. 1. Element 6 in FIG. 1 denotes one or more optical elements comprising a second set of transfer optics. The optical element(s) in the second set of transfer optics include, but are not limited to, lenses and mirrors of any shape, size, materials, and properties to direct the EM radiation. In one embodiment, the second set of transfer optics comprises a flat aluminum mirror and a ZnSe lens. The second set of transfer optics directs the EM beam towards the wavelength discrimination device 7. In one embodiment of the present invention, the wavelength discrimination device comprises a Fabry-Perot Tunable filter (FPTF), which contains a mobile reflective surface which allows the FPTF to act as a tunable filter whose bandpass wavelengths can be scanned, allowing spectra of samples at multiple wavelengths to be measured. (For clarity, a FPTF is not the same as a Fabry-Perot interferometer (FPI), which comprises two immobile partially reflective surfaces forming an optical cavity that transmits only a fixed bandwidth of wavelengths and cannot be scanned to change the set of bandpass wavelengths. Because a Fabry-Perot interferometer (FPI) cannot be scanned, it can only measure absorbance at one set of wavelengths.)

Figure 2A:
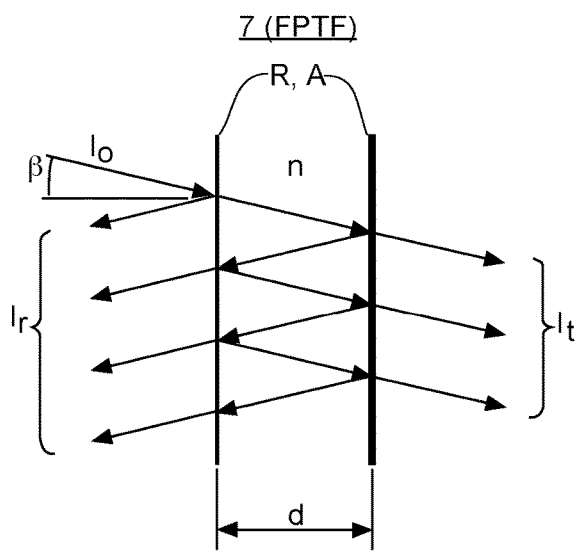
FIG. 2A shows a schematic of a Fabry-Perot Tunable Filter (FPTF) comprising two flat (one mobile) and partially transmitting, mirrors arranged in parallel at a given distance, forming an optical resonator with a given refractive index, according to one embodiment of the present invention. One of the mirrors can be moved to change the given distance between the mirrors to achieve wavelength scanability.

In a Fabry-Perot Tunable filter (FPTF), two flat and partially transmitting mirrors, characterized by reflectance R and absorptance A, are arranged in parallel at a distance d, forming an optical resonator with the refractive index n, as illustrated in FIG. 2A. One or both partially reflective surfaces may be moved, allowing d to vary, thereby allowing different bandwidths to pass. This allows absorbances at a plurality of wavelengths to be measured, giving a true spectrum comprising of a plurality of data points.

Figure 2B:
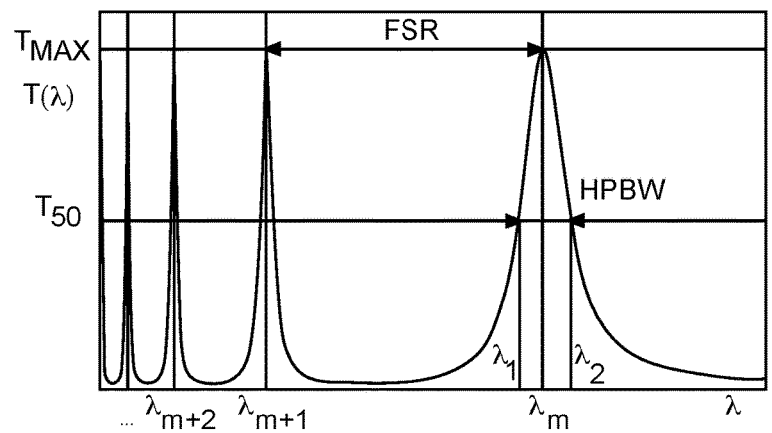
FIG. 2B shows a multiple-beam interference pattern of successive peaks of different orders in a transmittance spectrum of the FPTF, according to one embodiment of the present invention.
Figure 2C:
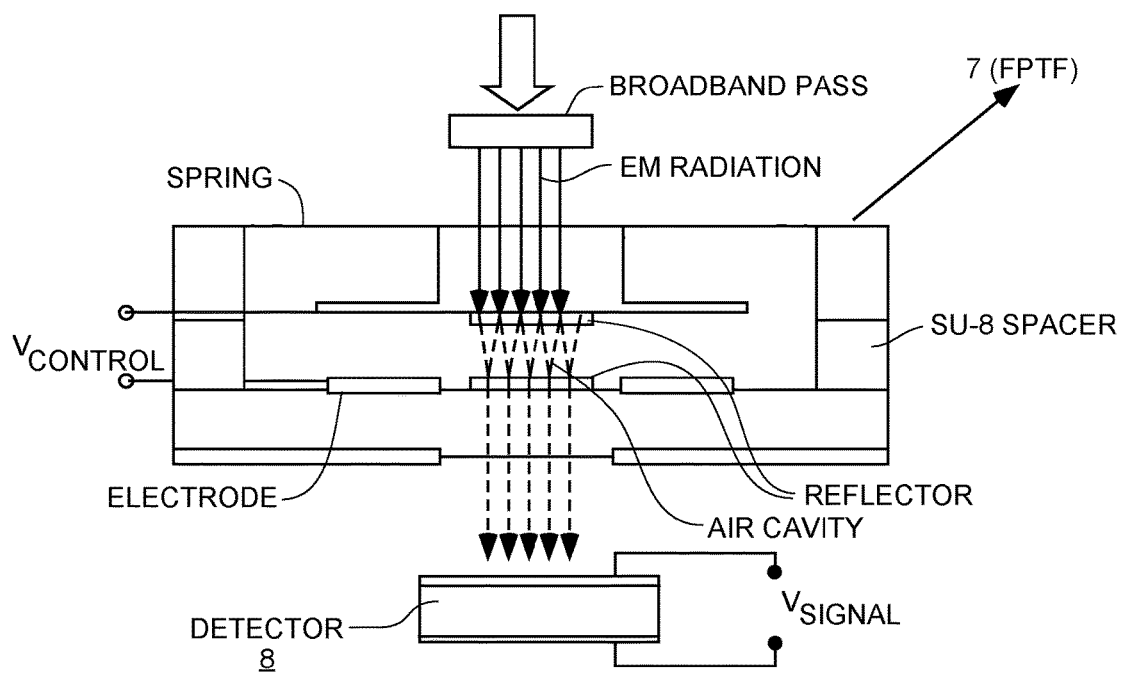
FIG. 2C shows a schematic of a Fabry-Perot Tunable Filter (FPTF), according to one embodiment of the present invention.

A reflective surface moving element is used to move the mobile reflective surface, as shown in FIG. 2C. In one embodiment, the mobile reflective surface has a spring attached to a back side of the mobile reflective element to allow EM radiation to pass. In one embodiment, a voltage is swept which electrostatically moves the mobile reflective surface, changing d, which gives it the ability to scan multiple bandpass wavelengths. Other examples of reflective surface moving elements include, but are not limited to, electric motors, direct drive motors, piezoelectric motors, and mechanical elements actuated by the motors, such as arms and levers.

For a Fabry-Perot tunable filter, the incident EM beam with intensity $I_0$ and wavelengths $\lambda$, incident under the angle $\beta$ in FIG. 2A, enters the optical resonator and is reflected back and forth. Multiple-beam interference generates a pattern of successive peaks in the transmittance spectrum $T(\lambda)$ of the FPTF (FIG. 2B), described by the Airy formula:

$$T(\lambda) = I_t/I_0 = T_{max}/(1 + F \sin 2Q) \quad (3)$$

where $$Q = 2\pi n d \cos \beta / \lambda \quad (4)$$

with the peak transmittance $$T_{max} = [1 - A/(1-R)]^2 \quad (5)$$

and the finesse factor $Ff$ $$Ff = 4R/(1-R)^2 \quad (6)$$

The transmittance peaks of different interference orders m are located at wavelengths for which the resonance condition is met:

$$\lambda_m = 2nd \cos \beta / m \quad (7)$$

Typically, m=1, or first order radiation is used.

The FPTF can be used as a tunable narrowband filter by varying the distance d between the parallel partially reflecting surfaces. If the desired order is selected by means of an additional broad bandpass filter (order sorting filter, blocking filter), the resonator gap d can be adjusted to tune the transmitted wavelength $\lambda_m$ within the given free spectral range FSR for this order. The characteristic filter parameters of an FPTF can be derived from the previous equations.

The center wavelength CWL is defined as the mean value of the two half-power-points (T50) in terms of wavenumbers:

$$CWL = 2\lambda_1\lambda_2/(\lambda_1+\lambda_2) \quad (8)$$

Because of the periodicity of the Airy formula in wavenumbers, calculation of the CWL in the wavenumber domain is preferred over wavelengths. In general, calculation of the CWL of interference filters in the wavenumber or wavelength domain can both be used. The half-power bandwidth HPBW is the decisive factor for the spectral resolution:

$$HPBW = 2d[(1-R)/\pi\sqrt{R}] \quad (9)$$

The ratio of FSR and HPBW (calculated in terms of wavenumbers) is called the finesse. In the theoretical ideal case (perfectly flat, smooth and parallel mirrors, collimated beam) it depends only on the reflectance R (reflectance finesse $F_R$):

$$F_r = FSR/HPBW = \pi\sqrt{R}/(1-R) = \pi\sqrt{Ff}/2 \quad (10)$$

In practice, the finesse is limited by imperfections of the mirrors and the angle distribution of the transmitted beam.

Element 8 in FIG. 1 comprises an electromagnetic radiation detector. One detector, a plurality of detectors, a detector array, a two-dimensional array, or any other arrangement of detectors may be used. A detector may include, but is not limited to, a pyroelectric detector, pyroelectric bolometer, photoconductor, photovoltaic, a photomultiplier, or a charge-coupled device. Detector element materials may comprise any material with a response to EM radiation whereby an electrical signal is generated. These materials may include, but are not limited to, deuterated triglycine sulfate, triglycine sulfate, lithium tantalate, mercury cadmium telluride, lead sulfide, silicon, germanium, indium antimonide, indium gallium arsenide, and indium arsenic antimonide. The detector should be sensitive to the EM wavelengths given off by the EM source 1. The EM beam impinging on detector 8 contains the spectral information of the spectrum of the sample that was in contact with IRE 3. Generally, the sample spectrum discloses how much EM amplitude was detected at a plurality of detected wavelengths. The sample spectrum may be combined with a background spectrum (a spectrum measured with no sample in contact with the IRE 3) to calculate an absorbance or transmittance spectrum [1]. The FPTF may be combined with the detector element(s) forming a unit. For multiple wavelength ranges, a plurality of FPTFs may be used.

In an exemplary embodiment, the FPTF-ATR spectrometer comprises an electrically pulsed mid-infrared source, a first set of transfer optics comprising a parabolic aluminum mirror and ZnSe lens transfer optics, a ZnSe IRE, manually actuated clamp with a slip-clutch mechanism, a second set of transfer optics comprising a flat aluminum mirror and a ZnSe lens, and an FPTF wavelength discriminator equipped with a lithium tantalate detector element. In this embodiment, the FPTF, the detector element, and the filter comprise a single unit.

In FIG. 1, element 9 denotes a communication element for communicating the signal containing sample information from the FPTF-ATR spectrometer to device(s) for controlling, analyzing data, and displaying data. This communication may take place via a wire or wirelessly. Analogue-to-digital conversion may be used, as needed, to convert analogue data from the detectors' signal to digital data for the controlling devices. The controlling device may issue commands to, receive information and data from, monitor, and control the spectrometer. The display device may be part of, or separate from, the controlling device, and may be used to display information about the spectrometer, such as its status, and display data including spectra. The analysis device may be part of, or separate from, the controlling and/or displaying device, and may be used to analyze spectra to, for example, to identify chemical species present in the sample, determine the amounts of chemical species in samples, or determine the properties of samples. The control device(s) may include, but not be limited to, a computer, tablet computer, or mobile phone. Communications between the spectrometer and control/analysis/display device(s) may be by wire or wirelessly.

In one embodiment, the FPTF-ATR spectrometer may be used to measure an amount of light absorbed by a sample at one or more wavelengths. The spectrum may then be used to identify what chemical species are present, determine any property of the sample, or quantify chemical species present. In one embodiment, spectra of standard samples are measured, and peak areas or heights may be plotted versus known concentration to obtain a calibration line, which can then be combined with the spectrum of an unknown sample to predict the sample's properties or concentrations of chemical species in a sample. In another embodiment, spectra of standard samples are measured and multivariate chemometric algorithms, including, but not limited to, Principal Components Analysis, Principal Components Regression, and Partial Least Squares, may be used to obtain a model. This model may then be combined with the spectrum of an unknown sample to classify it, identify the chemical species present, quantify chemical species in the sample, or predict any other sample property from the sample's spectrum.

In short, the present invention may be used to analyze any solid or liquid material by simply placing the sample in contact with the sampling surface of the IRE as seen at 5 in FIG. 1. Certain materials may require the application of pressure using the pressure application element 4.

Illustrative Applications of the Invention

In the last few years, a number of states in the U.S., as well as Canada, and other countries around the world, have legalized the use of medical and recreational *cannabis*, so there now exist legal articles of commerce based on the *cannabis* plant. Amongst the types of molecules found in *cannabis* are cannabinoids, terpenes, and moisture [6].

Cannabinoids are molecules that interact with the human body's endogenous cannabinoid receptors. Terpenes are molecules, commonly found in plants, containing one or more C=C bonds. Terpenes are typically volatile and have a strong smell and/or flavor. For example, the smell of citrus fruits or pine sap is due to terpenes. Terpenes are responsible for the smell and flavor of *cannabis* containing materials, and may be responsible for some of the *cannabis* user experience as well. Cannabis based articles of commerce include, but are not limited to, dried buds and all other parts of the *cannabis* plant. Also, there exist *cannabis* extracts which are made by using physical or chemical means to enhance the concentration of cannabinoids and/or terpenes in a material. These extracts go by various names including, but not limited to, concentrates, *cannabis* concentrates, oils, *cannabis* oils, processed oils, *cannabis* processed oils kief, resin, sugar, rosin, oils, butter, shatter, dabs, hash, bubble hash, and hashish.

"Edibles" are food items that have had *cannabis* or *cannabis* extracts added to them. Additionally, various tinctures, salves, ointments, lotions, oils etc. that have had *cannabis* or *cannabis* extracts added to them are articles of commerce. All these materials form a family of "*cannabis* containing materials" (CCMs). Like any other product that goes into or onto the human body, there exists a need to chemically characterize CCMs to establish their identity, quality, safety, potency, and efficacy. In one embodiment, the invention can be used to measure the presence and amount of cannabinoids, terpenes, moisture, and any other chemical compounds in *cannabis* containing materials.

Uses for the present invention in analyzing CCMS include, but are not limited to, determining potency, determining potency degradation rate and mechanism, monitoring, controlling, and optimizing *cannabis* grows, determining harvest time, optimizing growing conditions, determining best lighting conditions, monitoring and controlling a *cannabis* extraction process, classifying *cannabis* strains, distinguishing between medical and recreational marijuana, and determination of the safety and efficacy of *cannabis* based materials.

Further applications of the device include, but are not limited to, determining the potency of dried *cannabis* buds, and the cannabinoid and terpene profiles of *cannabis* containing materials. The device may be used by *cannabis* dispensaries at the point of sale to give on the spot analyses assuring customers of the potency and efficacy of the materials they are buying. The device may be used to examine *cannabis* plant parts to determine their sex, or find and eliminate bad plants. The device may be used by growers in the field to determine *cannabis* bud potency and optimize growing conditions. The device may also be used to sort *cannabis* buds by strain type, for example distinguishing between medicinal ("CBD") and recreational ("THC") strains, or distinguishing between species of marijuana plants such as indica, *sativa*, or hybrid.

In another embodiment, the present invention may be used to characterize *cannabis* concentrates. Uses include, but are not limited to, determining the chemical species present, predicting the properties, and quantitating the chemical species present. The device may be used at an extraction machine to monitor the extract product during and after its manufacture. In one embodiment, the device is used to determine the potency, cannabinoids, moisture, and terpenes in *cannabis* concentrates. In yet another embodiment, the present invention may be used to characterize *cannabis* containing edibles, lotions, tinctures, lotions, salves, and oils etc., including determining and quantitating chemical species and predicting sample properties.

The flowers of the hops plant are added to beer during the brewing process to add flavor and deter spoilage. The hop flower contains molecules called alpha acids and beta acids; and like *cannabis* plants, terpenes and moisture are also present. When hop flowers are harvested, they are analyzed for their alpha acid, beta acid, terpene, and moisture content. Additionally, properties called total oil and hop storage index are determined. Currently to perform this analysis involves a time consuming solid-liquid extraction using toluene. Toluene is expensive, smelly, flammable, toxic, and requires the use of a fume hood and special garments and gloves.

In one embodiment, the invention is used to obtain spectra of dried hops, dried hops combs, and pelletized hops, which will be referred to as "hops containing materials" (HCMs), without the need for toluene extraction. There is no sample preparation needed, so no use of toluene is required saving time, money, trouble, and toxicity. No fume hood or special garments are required. Spectra measured with the device may be used to categorize and characterize hops. The spectra may be used to determine the chemical species in hops. The spectra may be used to determine the amounts of chemical species in hops. In one embodiment, the peak areas or heights of peaks in the spectra can be used to obtain a calibration. In another embodiment, chemometric algorithms including, but not limited to, Principal Components Analysis, Principal Components Regression and Partial Least Squares may be used to obtain a calibration. The analytes quantitated may include but are not limited to alpha acids, beta acids, total oils, hop storage index, moisture, and terpenes.

Illustrative Embodiment

Without loss of generality, an illustrative embodiment is now described. Element numbers refer to elements in FIG. 1.

Figure 3:
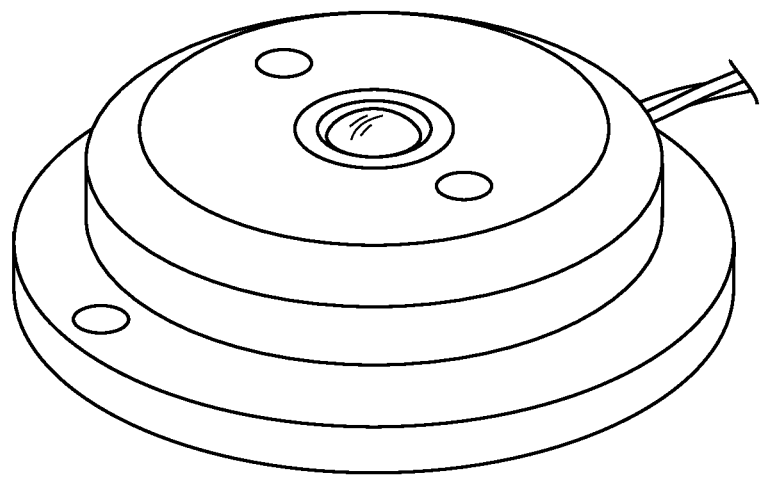
FIG. 3 shows an electromagnetic ("light") source of the device mounted in its housing, according to one embodiment of the present invention.

The electromagnetic radiation (light) source 1 is a resistively heated element that emits mid-infrared (IR) light. It is mounted in a housing as seen in FIG. 3. FIG. 3 shows the light source mounted in its housing. The source housing is attached to the side of the optics module (the box) as seen in FIG. 4.

Figure 4:
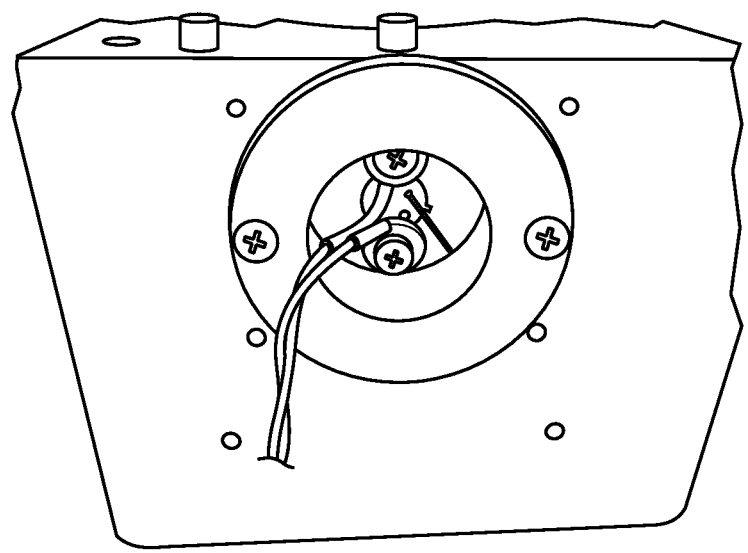
FIG. 4 shows the light source housing attached to a side of an optics module of the device, according to one embodiment of the present invention.

FIG. 4 shows the source housing attached to the side of the optics module. The wires in FIG. 4 supply power to the source. The source is approximately centered on the optics module input iris, and is placed several mm inside this iris. The source is pulsed at a frequency of 10 Hz, range 6.25 to 500 Hz. It is powered at 85 milliamps, range 1-200 milliamps. The source gives off light in the mid-infrared, including from 1250 to 952 cm'. Once emitted by the source the mid-infrared light beam impinges on a transfer optic or optics 2, typically a flat mirror or a parabolic mirror and ZnSe lens. A picture of two flat aluminum mirrors that comprise part of the transfer optics are seen in FIG. 5.

Figure 5:
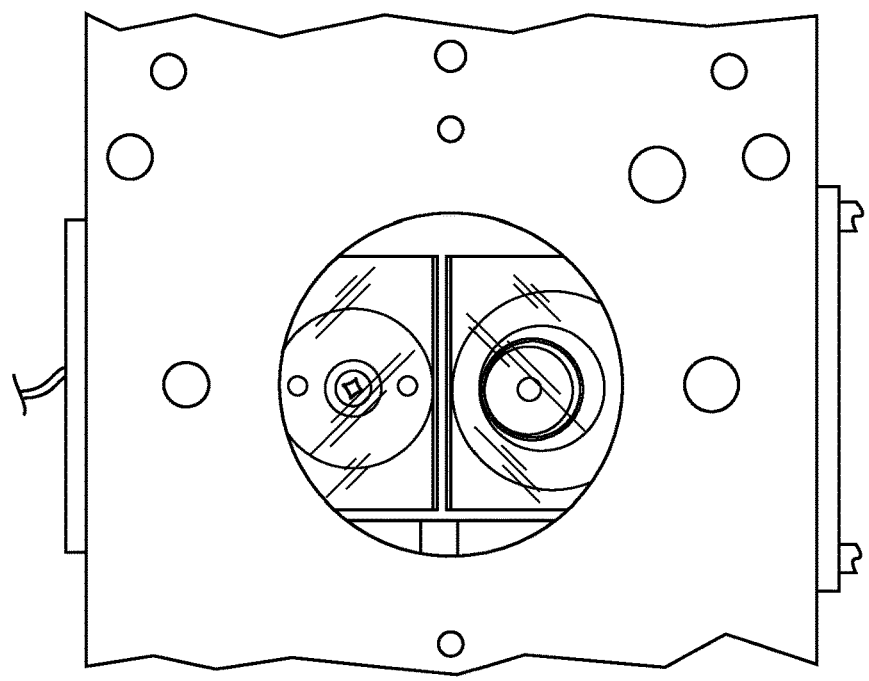
FIG. 5 shows a transfer optics in the optics module of the device as viewed from above, according to one embodiment of the present invention. The elements seen in the transfer optics window are of the electromagnetic source and Fabry-Perot tunable filter.

FIG. 5 shows part of the transfer optics as viewed from above. Left shows part of the first transfer optic, a flat aluminum mirror. Right shows part of the second transfer optic, a flat aluminum mirror. The image on the left is the light source. The image to the right is the Fabry-Perot tunable filter (FPTF). Upon reflection from the first transfer optics, the infrared beam impinges on a surface of an internal reflection element (IRE) 3. Typically the IRE is made from zinc selenide (ZnSe), may be made from diamond, or a combination of a ZnSe focusing lens and a diamond IRE, or a combination of a ZnSe focusing lens and ZnSe IRE. The IRE may be contained in a holder or bracket. A picture of the bottom of a ZnSe IRE focusing lens in a holder is seen in FIG. 6.

Figure 6:
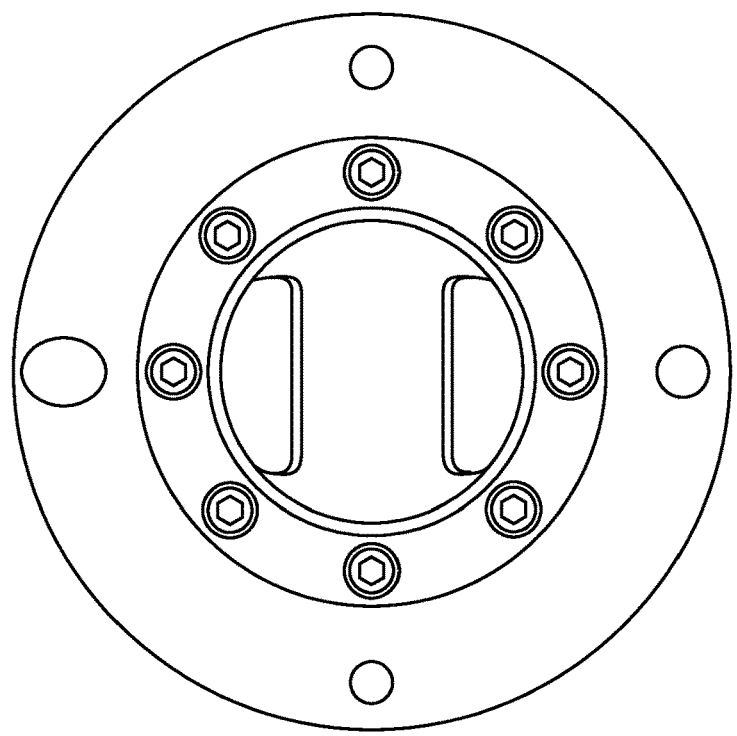
FIG. 6 shows a bottom side of an internal reflection element (IRE) lens of the device in its bracket, according to one embodiment of the present invention.

FIG. 6 shows the bottom side of a ZnSe IRE focusing lens in a bracket. The infrared beam enters the aperture to the left and exits from the aperture to the right. After leaving the IRE, the infrared beam impinges upon a second set of transfer optics 6. Typically this is a flat aluminum (Al) mirror and ZnSe lens as seen in FIG. 6. The second set of transfer optics directs the IR beam so that it impinges upon a Fabry-Perot Tunable filter (FPTF) 7, which acts as a wavelength selector.

The FPTF comprises two parallel partially reflective surfaces forming an optical cavity. The distance between these surfaces can be varied, allowing different bandpass wavelengths to pass and allowing for the measurement of a spectrum at a plurality of wavelengths. This light then impinges upon an electromagnetic radiation detector 8. Typically this is a lithium tantalate detector element that is combined in one package with the FPTF. An illustration of this package mounted in a circuit board is seen in FIG. 7.

Figure 7:
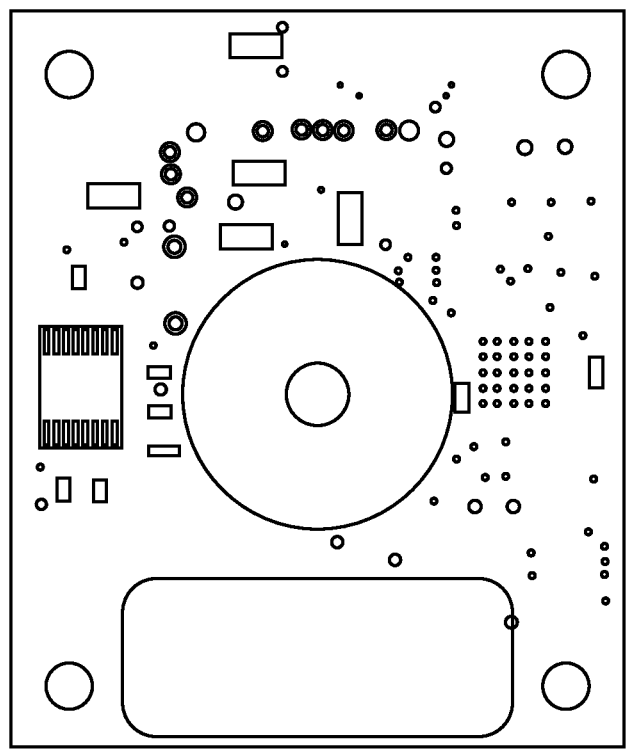
FIG. 7 shows a circular FPTF electronics package installed on a circuit board which contains a wavelength selector and detector of the device, according to one embodiment of the present invention.

FIG. 7 shows a circular aluminum electronics package or "can" in the middle which includes the FPTF 7, which also contains the detector 8. This assembly is mounted on a printed circuit board.

Illustrative FPTF operational and scanning parameters are shown below:

1. Wavenumber: For *cannabis* containing materials, the 1250-952 cm' range was used. Other ranges may be used for other types of samples.
2. Step Size: Range of 20 to 1000 nm, exemplary value of 100 nm.
3. Single spectra can be measured of a sample and quantitated, or multiple spectra can be measured, and the quantitative results averaged. The number of spectra to average can be any integer greater than 1, exemplary value is 3.
4. There is a test built into the software whereby the amount of analyte predicted from a sample spectrum is compared to the amount range used in the calibration, and an error message is printed if the analyzed sample is outside that range. Any amount of concentration unit may be used for quantitation. Exemplary values will depend upon the analyte.
5. Gain: An amplifier can be used to increase the size of the FPTF signal using a gain setting. Range of 0.82-1000, exemplary value of 1.0.
6. Offset: A voltage added to the FPTF signal. Range of 0 to 5 millivolts, exemplary value of 0.5 millivolts.
7. Duty Cycle: Affects depth and amplitude of FPTF Signal. Range of 0-100%, exemplary value of 60%.
8. Number of signals: At each scanned wavelength, there is the ability to add together a number of measurements to help increase signal-to-noise ratio. Range of 1-16, exemplary value of 16.
9. Settling Time: The amount of time the FPTF is allowed to settle between individual measurements. Range of 1-1000 milliseconds, exemplary value of 125 milliseconds.

The FPTF is typically run in first-order, with an order sorting filter integral to the FPTF package. The typical cone angle of the incoming infrared beam is typically ±3°, but may be as high as ±15°. The absorptance of the cavity is low because it consists of air. The reflectivity of the surfaces defining the optical cavity are typically 0.9 to 0.97.

The half-power bandwidth (HPBW), a measure of spectral resolution, depends upon the center wavelength and the specific detector being used. Typical values are 130 to 220 nm. In practice finesse (fF), values of 20 to 100 can be achieved.

The FPTF/circuit board assembly is mounted on a bracket attached to the side of the optics module. An illustration of this bracket attached to the optics module is shown in FIG. 8.

Figure 8:
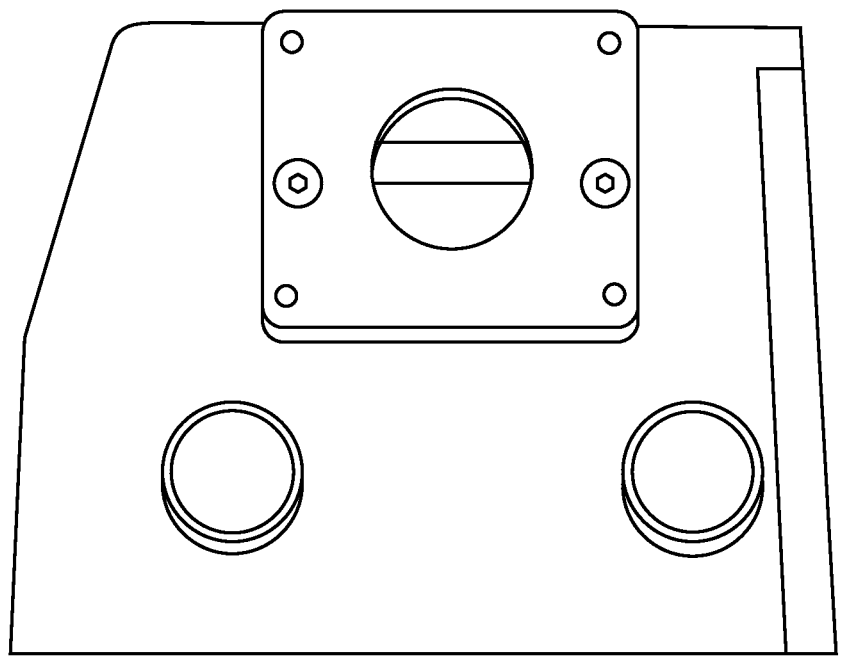
FIG. 8 shows a FPTF circuit board bracket attached to one side of the optics module of the device, according to one embodiment of the present invention.

FIG. 8 shows the FPTF circuit board bracket attached to the side of the optics module. The FPTF circuit board has mounting holes that are used to attach the board to its bracket with screws as shown in FIG. 9.

Figure 9:
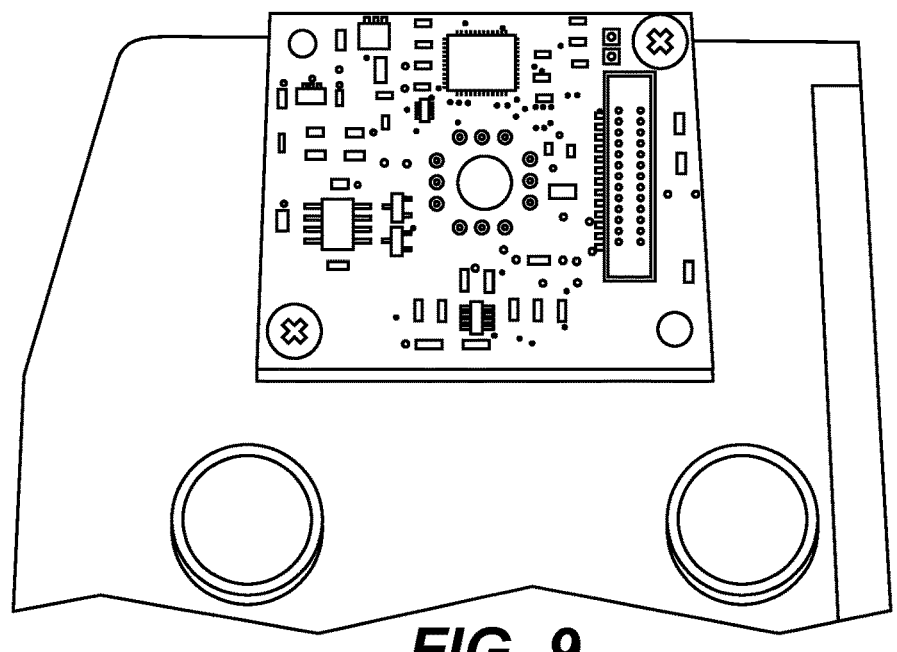
FIG. 9 shows a back of the FPTF circuit board mounted on the optics module of the device, according to one embodiment of the present invention.

FIG. 9 shows the back of the FPTF circuit board mounted on the optics module. The FPTF is approximately centered in the optics module output iris. The electrical signal from the FPTF is coupled to an analysis/display/output device 9, which is typically a personal computer. An assembled spectrometer module with the source in its bracket, the FPTF printed circuit board with the FPTF installed, and the IRE in place is shown in FIG. 10.

Figure 10:
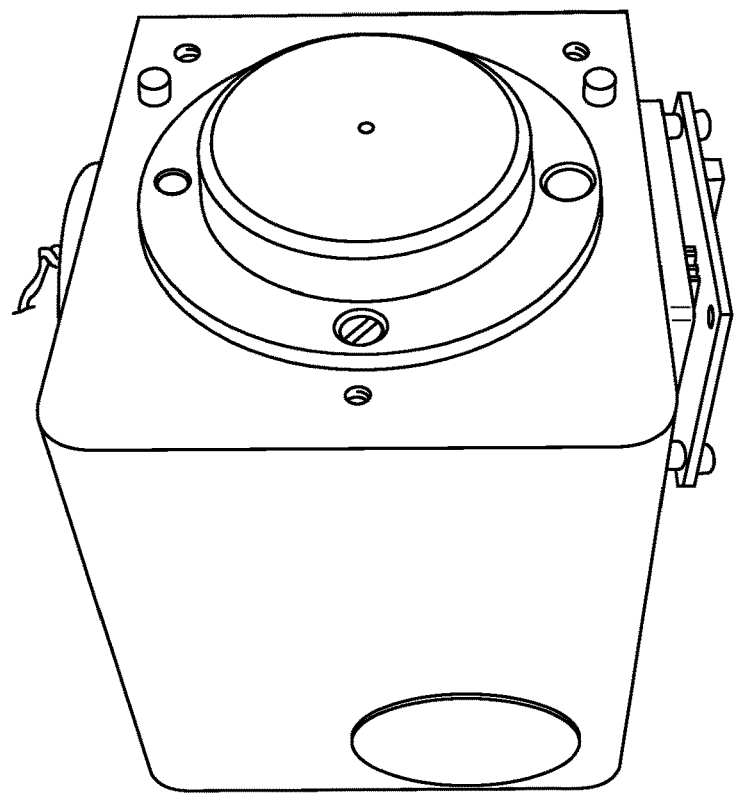
FIG. 10 shows an assembled spectrometer module with the light source in its housing, an IRE sampling surface, and the FPTF circuit board mounted in place on its bracket on the optics module, according to one embodiment of the present invention.
Figure 11:
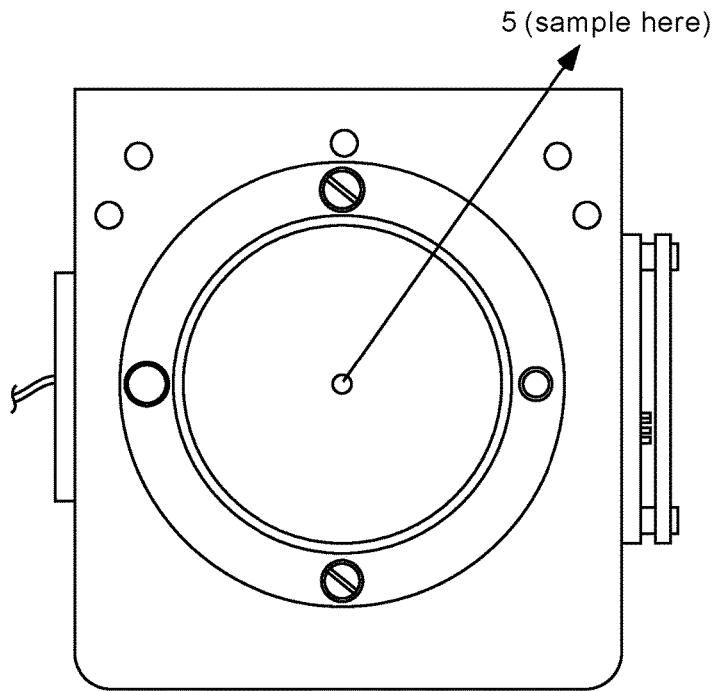
FIG. 11 shows the IRE housed in a stainless-steel puck bracket, with the center of the puck being located where the samples are placed, according to one embodiment of the present invention.

FIG. 10 shows an assembled spectrometer module with the source, the IRE, and the FPTF board mounted in place. Wires and circular bracket to left are used to mount the electromagnetic source 1. The circular "puck" on the top houses the IRE 3. The dot in the center in the top of the IRE is where samples are placed. The bracket and printed circuit board to the right are used to mount the FPTF wavelength selector 7 and detector 8. The IRE is typically housed in a stainless-steel housing that looks somewhat like a hockey puck, and is placed on top of the optics module as shown in FIG. 11. (See FIGS. 23-26 for illustrative CAD diagrams of the component parts of the FPTF-ATR spectrometer, according to just one embodiment of the present invention.)

Figure 12:
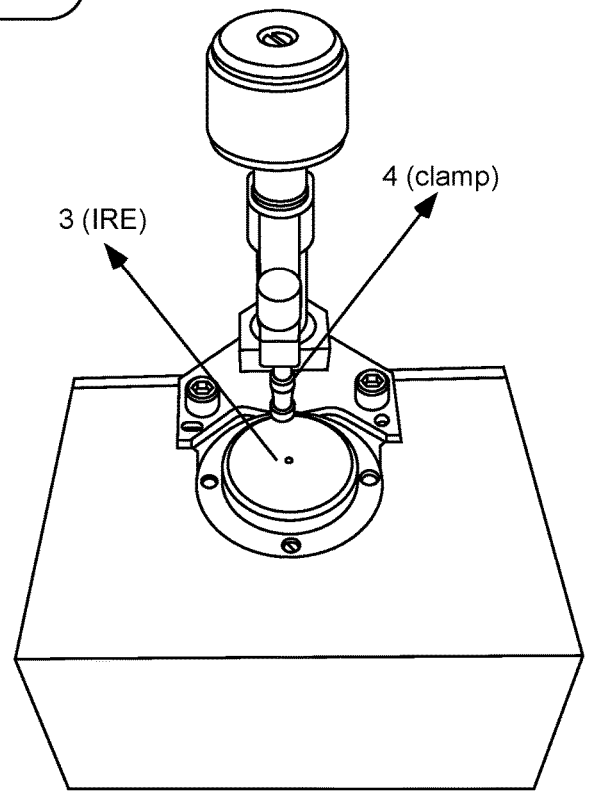
FIG. 12 shows a fully assembled FPTF-ATR spectrometer ("device"), according to one embodiment of the present invention.

FIG. 11 shows the IRE housed in a stainless steel "puck." The dot in the center of the puck is the sampling surface where samples are placed as indicated in FIG. 12.

FIG. 12 shows a fully assembled FPTF-ATR spectrometer. Element 3 is a sampling surface of the internal reflection element where samples are placed to interact with the evanescent wave. Element 4 is a sample clamp of the slip clutch variety. The FPTF-ATR spectrometer can be used to acquire spectra and thus analyze any sample that can be brought into contact with a sampling surface. A close-up of the spectrometer analyzing a *cannabis* oil sample is seen in FIG. 13.

Figure 13:
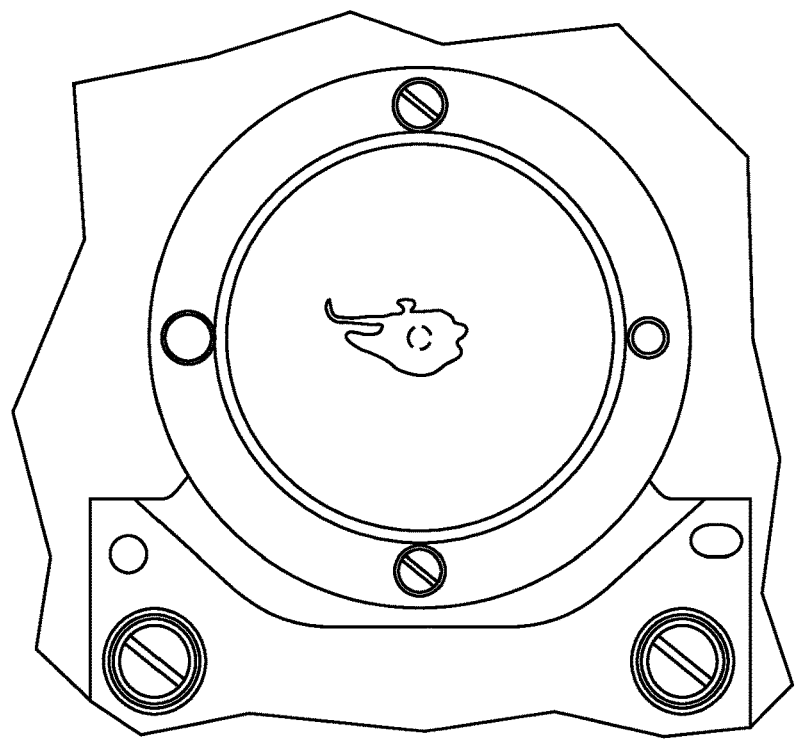
FIG. 13 shows a close-up of a *cannabis* oil sample sitting on a sampling surface of the IRE of the device, according to one embodiment of the present invention.

FIG. 13 shows a close-up of a *cannabis* oil sample sitting on the sampling surface of the IRE. For liquids of low viscosity, a drop or two can be placed on the sampling surface and allowed to flow to cover the surface of the IRE for analysis. Traditionally it was thought that pressure should not be applied to liquids since it might cause them to squirt to the side away from the presence of the evanescent wave [1].

However, it has since been discovered for viscous liquids, things that might have the consistency of saltwater taffy, the fluid will not flow enough in a reasonable time to cover the entire sampling surface and hence not make good contact with the evanescent wave, which is important for measuring accurate spectral peak heights, and hence obtaining accurate predicted concentrations. Thus, contrary to the literature, the inventors have found that for these types of fluid samples, applying pressure using the clamp makes them flow, yielding good contact with the evanescent wave, yielding quality spectra for spectral analysis.

Figure 14:
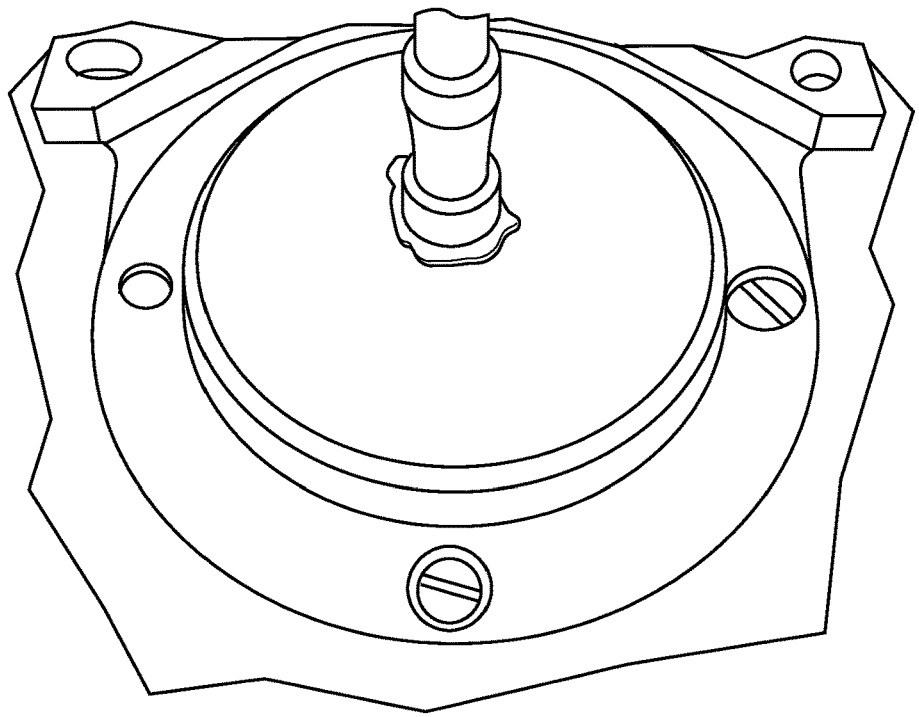
FIG. 14 shows a *cannabis* shatter sample being held to a sampling surface by a clamp tip of the device, according to one embodiment of the present invention.

FIG. 14 shows a *cannabis* shatter sample being held to the sampling surface by a clamp tip. This sample would not flow sufficiently when placed on the sampling surface to allow a spectrum to be measured, but flowed under pressure from the clamp to make sufficient contact with the evanescent wave to obtain a quality spectrum. This is an example of the type of fluid sample that requires pressure application.

Figure 15:
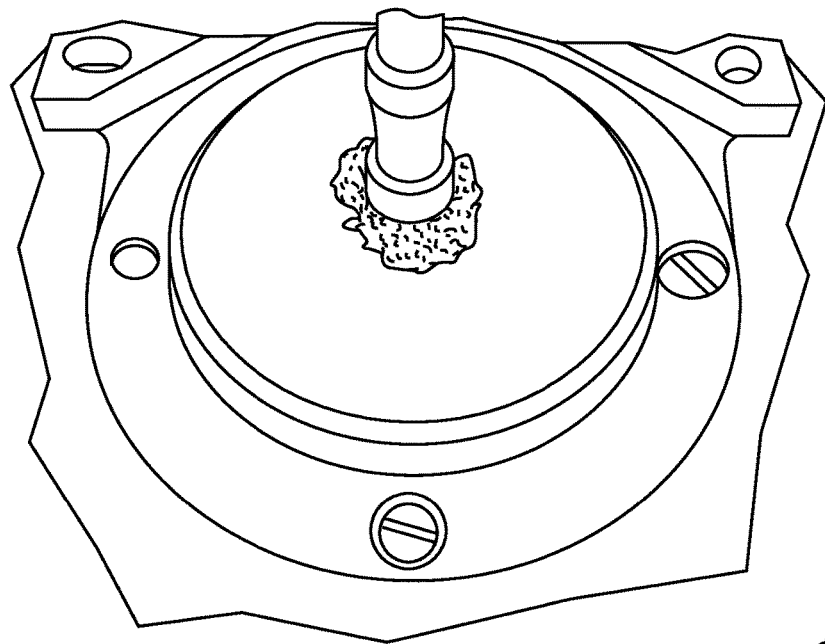
FIG. 15 shows a close-up of a clamp holding a marijuana bud sample to a sampling surface of the device, according to one embodiment of the present invention.

The FPTF-ATR spectrometer may also be used to obtain spectra of solids. In general, solids will need to have pressure applied to them using a pressure application element, such as a clamp, to make good contact with the sampling surface so the sample interacts properly with the evanescent wave. This is illustrated in FIG. 15, which shows a *cannabis* bud being analyzed with a clamp holding it to the sampling surface. FIG. 15 shows a close-up of a clamp holding a marijuana bud sample to the sampling surface. A pressure application element for applying pressure to some samples is needed to insure good contact with the evanescent wave. The pressure applied needs to be repeatable so that reproducible spectra of samples can be obtained. A typical way of applying pressure is to use a slip-clutch clamp 4, similar to the one shown in FIG. 16.

Figure 16:
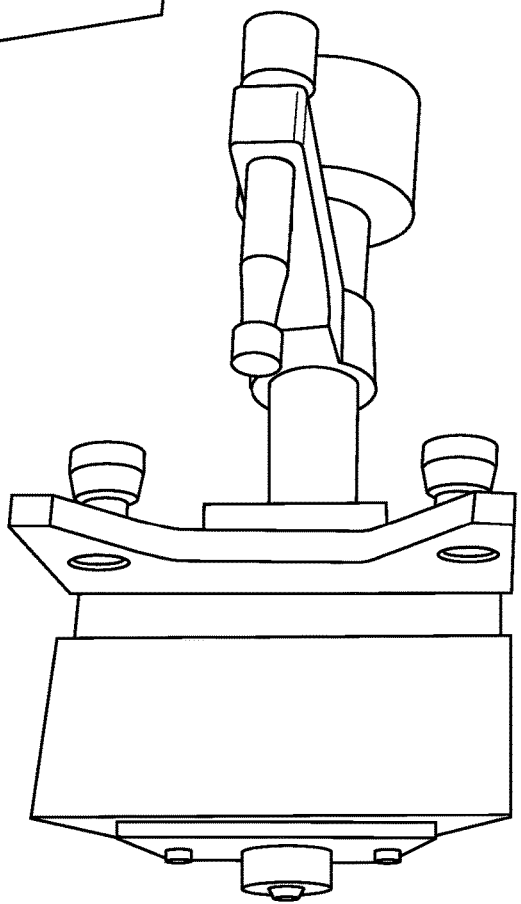
FIG. 16 shows a sample clamp of the slip-clutch variety in isolation, used to apply pressure to some samples, according to one embodiment of the present invention.

FIG. 16 shows a sample clamp of the slip-clutch variety by itself, used to apply pressure to some samples. A way of applying reproducible pressure to a sample is to use a clamp equipped with a "slip-clutch" mechanism. In this embodiment, turning the knob at the top clockwise will lower the clamp tip to compress the sample against the sampling surface. At a pre-set pressure, the knob will slip, not allowing any more pressure to be applied to the sample. The pressure setting at which the knob slips is typically 7 to 12 pounds per square inch (psi).

Illustrative Spectra

Figure 17:
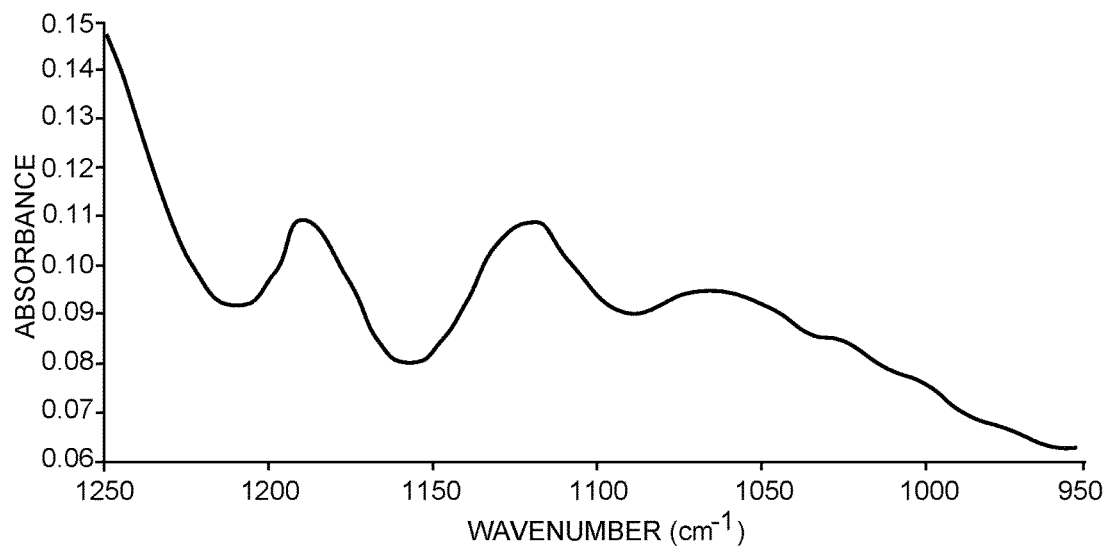
FIG. 17 shows an infrared spectrum of a marijuana bud sample measured with the FPTF-ATR spectrometer, according to one embodiment of the present invention.
Figure 18:
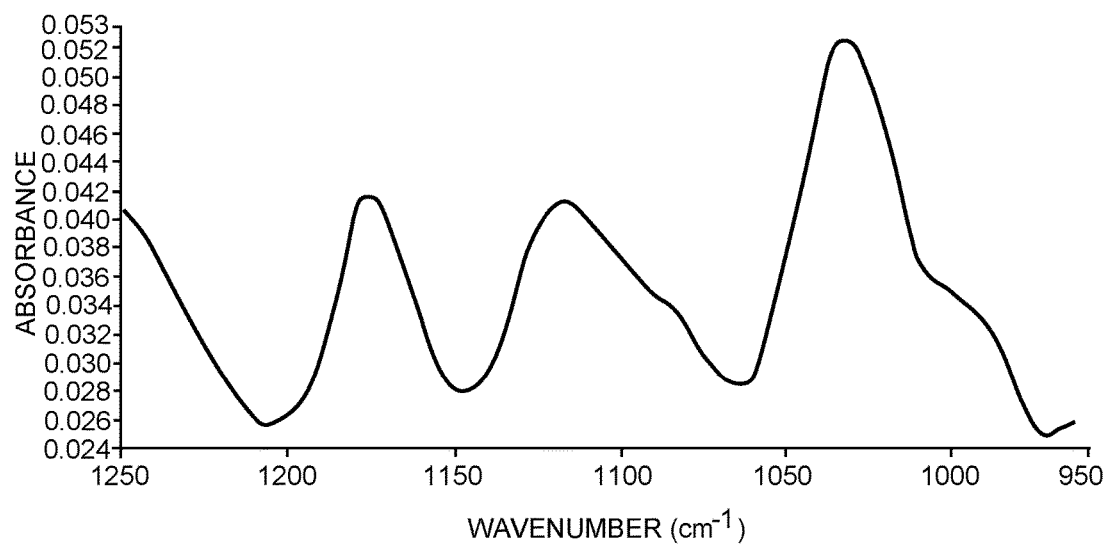
FIG. 18 shows an infrared spectrum of a *cannabis* oil sample measured with the FPTF-ATR spectrometer, according to one embodiment of the present invention.
Figure 19:
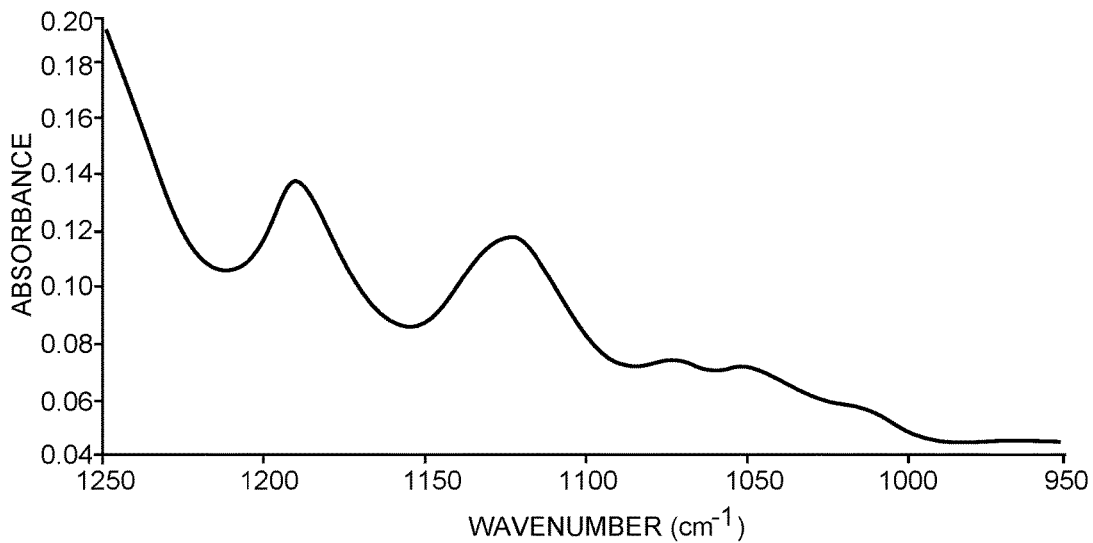
FIG. 19 shows an infrared spectrum of a *cannabis* shatter sample measured with the FPTF-ATR spectrometer, according to one embodiment of the present invention.

The FPTF-ATR spectrometer can be used to take spectra of any material that can be brought into contact with the sampling surface. In one embodiment, the spectrometer is used to analyze *cannabis* containing materials as illustrated with the following three spectra. FIG. 17 shows the infrared spectrum of a marijuana bud measured with a FPTF-ATR spectrometer. FIG. 18 shows the infrared spectrum of a *cannabis* oil measured with a FPTF-ATR spectrometer. FIG. 19 shows the infrared spectrum of a *cannabis* shatter sample measured with an FPTF-ATR spectrometer.

Figure 20:
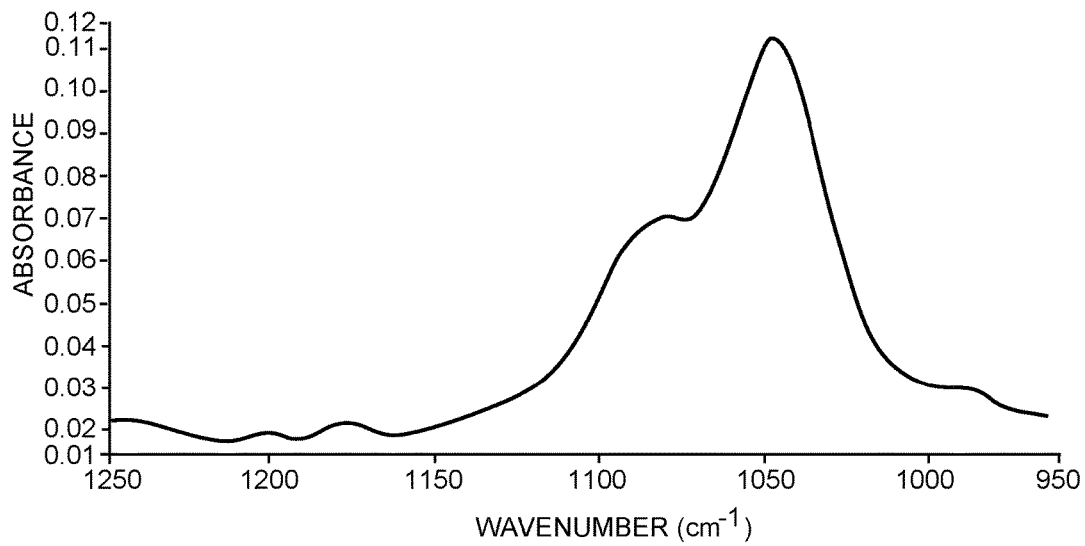
FIG. 20 shows an infrared spectrum of an ethanol containing hand sanitizer sample measured with the FPTF-ATR spectrometer, according to one embodiment of the present invention.
Figure 21:
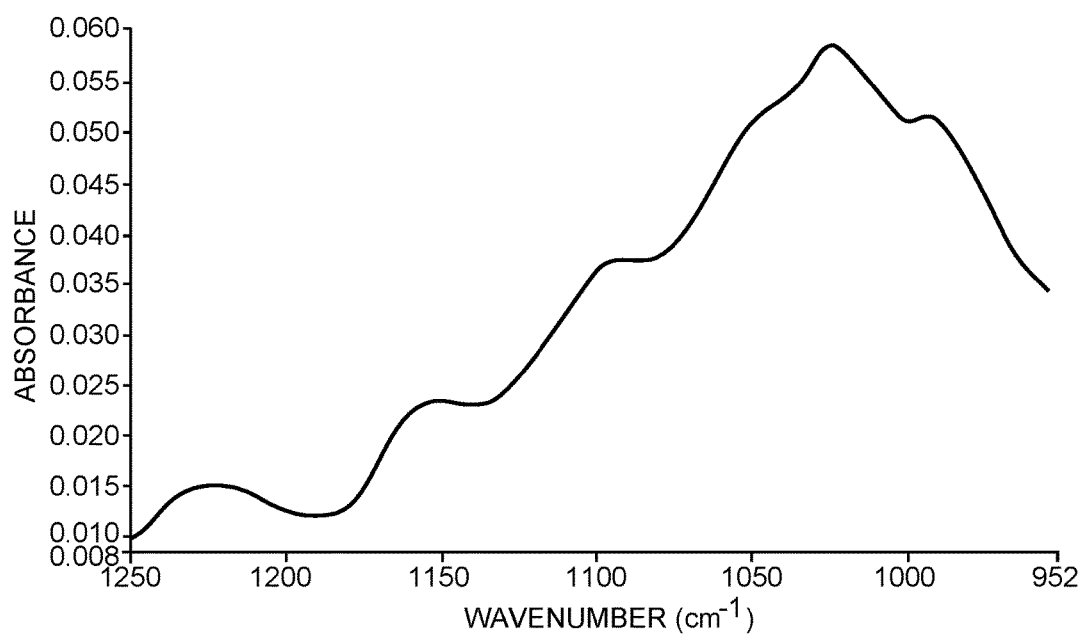
FIG. 21 shows an infrared spectrum of a paper towel measured with the FPTF-ATR spectrometer, according to one embodiment of the present invention.

The FPTF-ATR spectrometer may also be used to take spectra of non-*cannabis* containing materials. A wide variety of different samples can be analyzed using the FPTF-ATR spectrometer invention. For example, FIG. 20 shows the infrared spectrum of an ethanol containing hand sanitizer sample measured with an FPTF-ATR spectrometer. FIG. 21 shows the infrared spectrum of a paper towel measured with an FPTF-ATR spectrometer.

Spectral Analysis Details

The structure of molecules can be determined from their infrared spectra [2]. Briefly, infrared spectra can be interpreted to determine molecular structures from first principles, example spectra, and library searching.

An infrared spectrum may be used to determine the amount of one or more chemical species in a sample [3]. Briefly, the peak height or peak area in an infrared spectrum is proportional to concentration as related by Beer's Law, where:

$$A = \varepsilon l c \quad (11)$$

where
  $A$=absorbance, a measure of peak area or height,
  $\varepsilon$=the absorptivity, a physical constant for a pure material at a given wavelength under standard conditions,
  $l$=pathlength, the thickness of sample seen by the infrared light beam; exemplary value is 1 micron, which is determined by the design of the FPTF-ATR spectrometer and IRE, and
  $c$=concentration of analyte in appropriate units including, but not limited to, weight percent, mole percent, moles per volume, weight per volume, weight, and mass.

To establish a simple single analyte Beer's Law calibration, typically spectra of standard samples with known concentrations of the analyte are measured. Next, a peak in the spectrum whose size varies with analyte concentration is identified. The absorbance of this peak, determined as a peak height or area, is then measured. Then, a plot of absorbance versus concentration is made. According to Beer's Law, this plot, called a calibration line, should be a straight line with a slope of $\varepsilon l$. The spectrum of a sample with an unknown amount of the analyte can then be measured, its absorbance determined, and the concentration of analyte predicted in the unknown using the following equation:

$$C_{unk} = A_{unk} / \varepsilon l \quad (12)$$

where
  $C_{unk}$=concentration of analyte in the unknown sample,
  $A_{unk}$=absorbance of the unknown sample, and
  $\varepsilon l$=slope of the calibration line.

Note that a calibration should never be used on samples whose concentration falls outside the concentration range used in the calibration. For example, if a calibration goes from 20% to 80% analyte, results outside this range obtained on any sample are not legitimate and should not be reported. This is because the calibration should never be extrapolated into concentration ranges for which there is no data.

The calibration line approach works well for simple chemical systems, such as a single chemical species dissolved in a solvent. However, one of the assumptions in this method is that the peak whose absorbance is used is due only to the analyte. However, in complex systems, such as *cannabis* containing materials, there are many different molecules, each with numerous peaks that often overlap, so it becomes difficult to find a single peak that is due solely to a single analyte. The spectra of the different analytes in this case are said to interfere with each other.

One way around this problem is to use sophisticated statistical algorithms known as multivariate analysis algorithms, sometimes also called chemometric methods. "Chemometrics" is the application of multivariate algorithms to chemical data. Briefly, chemometric algorithms get around the interference problem by using up to an entire spectrum in the analysis rather than just one peak, and using many standard samples [3]. In one embodiment, the Partial Least Squares multivariate chemometric algorithm is used.

Figure 22:
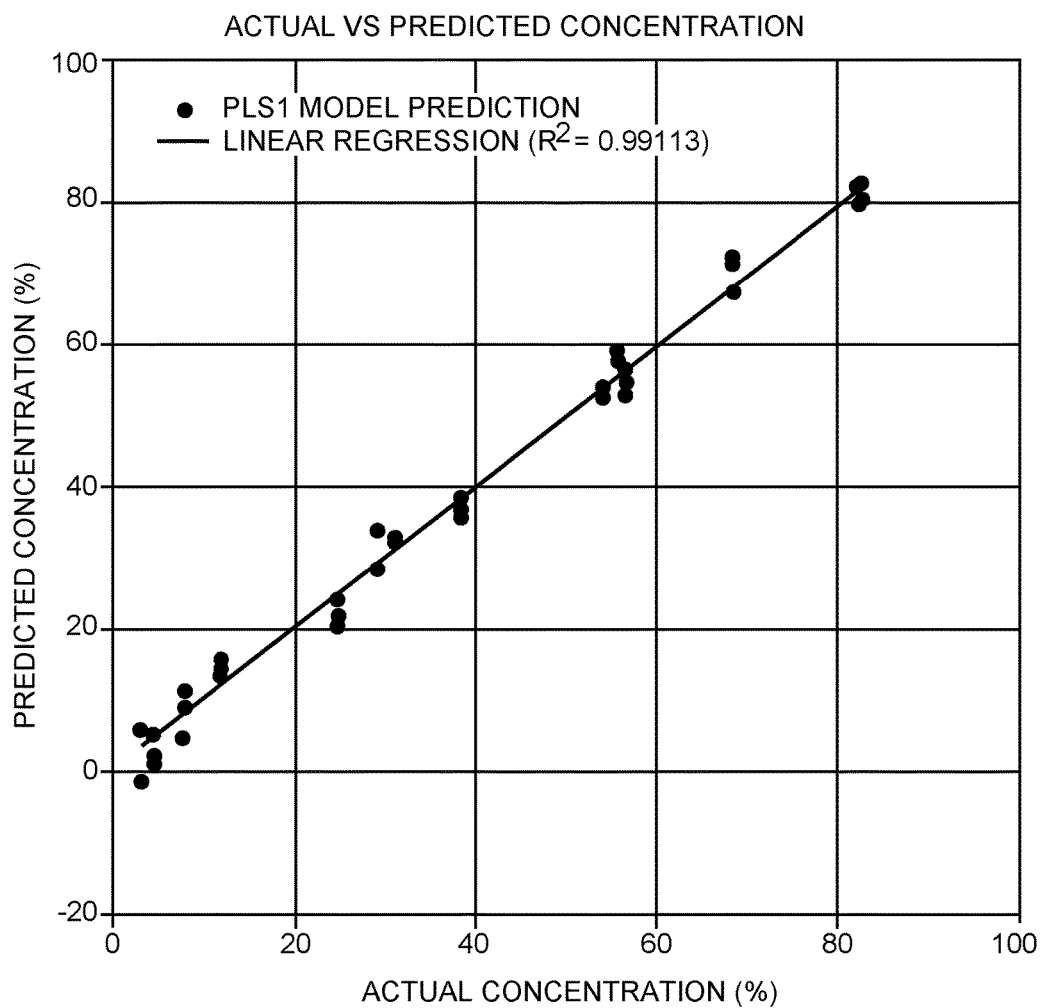
FIG. 22 compares modeled versus measured potencies of several *cannabis* oil samples, according to one embodiment of the present invention.

A measure of chemometric calibration quality is a plot of the reference amounts of the analyte as supplied by standards versus the analyte amount in the same samples as predicted by a spectroscopic chemometric model. For such plots, the correlation coefficient $R^2$ is a measure of model quality. It is measured on a 0 to 1 scale, where 1 is a perfect model (never achieved) and 0 means there is no correlation between the variables being plotted. $R^2$ is also a measure of the fraction of variance spanned by the model—the more the better. In spectroscopic analysis, $R^2$ values of 0.8 are usable, >0.9 are good, >0.99 are excellent. FIG. 22 is an example of such a plot for total tetrahydrocannabinol (total THC, a measure of potency) for *cannabis* oils. Total THC is the sum of the amounts of THC and Tetrahydrocannabinolic Acid (THCA) in a sample. These results are equivalent to those obtained on much larger, more expensive, bulkier, and difficult to use laboratory spectrometers [7].

FIG. 22 compares the modeled versus the actual weight percent Total THC for several *cannabis* oil samples. In FIG. 22, the x-axis shows the weight percent total THC in a set of *cannabis* oil samples as determined by High-Pressure Liquid Chromatography, while the Y-axis shows the weight percent total THC as determined from infrared spectra of the same samples measured with the present invention and application of a chemometric model. Note that the $R^2$ value for this plot is 0.99113, indicating excellent agreement between the two data sets, and that the present invention does an excellent job of predicting potency in *cannabis* oils. The following describes how the model whose results were used to generate FIG. 22.

Standard samples of 14 different *cannabis* oils had their weight percent total THC determined by High-Pressure Liquid Chromatography (HPLC). The total THC values determined ranged from 3.1 to 82.7 weight percent. Infrared spectra of these same samples were measured using the present invention, the FPTF-ATR spectrometer, from 1250 to 952 cm$^{-1}$ and step size of 100 nm. Three spectra of each sample were measured and used in the analysis. The spectra were pre-treated by applying a Pt derivative Savitsky-Golay algorithm, $2^{nd}$ degree polynomial, and 3 smoothing points [3]. The first derivative removes unwanted offset across the spectral data set.

The chemometric model was built from the infrared spectra of the standards and their known total THC weight percent as determined by HPLC. The Partial Least Squares 1 algorithm was used, and in the final analysis it was determined that using two principal components gave the best model.

The cross validation standard error of prediction (CVSEP) is a measure of chemometric model accuracy. It is calculated by taking a sample out of the calibration set, performing a calibration without it, and then applying that calibration to the spectrum of the left-out sample to predict analyte(s) concentration(s) or properties. The difference between the known and predicted concentrations or property is calculated. This process is performed in turn for every standard, and the CVSEP is related to the root mean square difference between the actual and predicted values for each sample. The CVSEP for the model used to generate FIG. 22 was 2.9 weight percent total THC.

Typically, spectra of three separate aliquots of the same sample are obtained, three different concentrations are predicted, and then the average is calculated. When this is done for total THC in *cannabis* oils, the CVSEP drops to below 2 weight percent. In general, averaging reduces the random noise in a measurement by the square root of the number of measurements added together. The square root of 3 is 1.7. Generally, this much improvement is seen in CVSEPs upon averaging three data points measured on three separate aliquots of the same sample.

In a similar fashion, models for other cannabinoids including, but not limited to, Tetrahydrocannabinol (THC), Tetrahydrocannabinolic Acid (THCA), Cannnabidiol (CBD), Cannabidiolic Acid (CBD), Total CBD (=CBDA+CBD), Cannabigerol (CBG), Cannabigerolic Acid, Total CBG (=CBGA+CBG), and Cannabinol (CBN) have been built. These cannabinoids can be determined in any *cannabis* containing material including, but not limited to, marijuana buds, *cannabis* liquids such as oils and extracts, and *cannabis* solids such as shatter, resin, rosin, sugar, wax, kief, and hashish. CVSEPs of better than 2 weight percent are achievable, typically with averaging of triplicate predicted values. Correlation coefficients from 0.9 to 0.99 are achievable.

The present invention can also be used to determine terpenes in *cannabis* containing materials including, but not limited to, marijuana buds, *cannabis* liquids such as oils and extracts, and *cannabis* solids such as shatter, resin, rosin, sugar, wax, kief, and hashish. Examples of terpenes that have been quantitated using the present invention include, but are not limited to, beta-caryophyllene, limonene, alpha-pinene, beta-pinene, cis- and trans-ocimene, myrcene, linalool, fenchol, alpha terpineol, nerol, geraniol, alpha humulene, cis- and trans-nerolidol, caryophyllene oxide, and alpha-terpinene. Correlation coefficients from 0.8 to 0.99 are achievable. CVSEPs of 0.1 weight percent are achievable.

Many other types of chemical species in many other types of samples may be identified and quantitated by infrared spectroscopy using the present invention. In addition, the properties of many types of samples can be determined from the FPTF-ATR spectra, such as the classification of marijuana plant strains and species based on the FPTF-ATR spectra of their dried flowers.

The present invention includes a means for determining whether a given unknown sample's predicted analyte amount is outside the calibration range; in this case a warning message is displayed to the user and the result is discarded. The present invention also has the ability to determine whether a chemometric model is applicable to a given sample's spectrum. This is used, for example, to warn when a cannabinoid model is about to be applied to a non-*cannabis* containing material. This means test uses the Mahalanobis distance average of the standard samples and the Mahalanobis distance of the analyzed sample compared to this number.

Infrared spectra and chemometric methods can not only be used to determine concentrations of chemical species, but can also be used to predict sample properties based on chemical composition, such as octane number, pH, and viscosity. The present invention could be used for many different types of sample property work.

Multivariate chemometric algorithms can also be used to classify samples based on their spectra. For example, an incoming raw material at a chemical plant could be classified as being the correct or incorrect material based on its measured spectrum and application of an appropriate multivariate chemometric model. Spectra measured using the current invention have been used, along with an appropriate Principal Components Analysis model, to differentiate between recreational and medicinal strains of *cannabis* plants based on the spectra of their dried buds. The current invention can also be used to determine the species of marijuana plants based on the spectra of their dried buds.

Many other types of examples of how the FPTF-ATR spectrometer can be used for classification would be evident to one of ordinary skill in the art.

Conclusions

Figure 23:
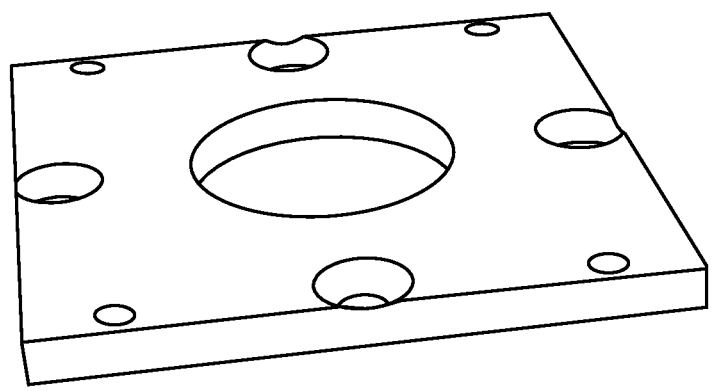
FIG. 23 shows a CAD diagram of a FPTF circuit board bracket for the FPTF-ATR spectrometer, according to one embodiment of the present invention.
Figure 24:
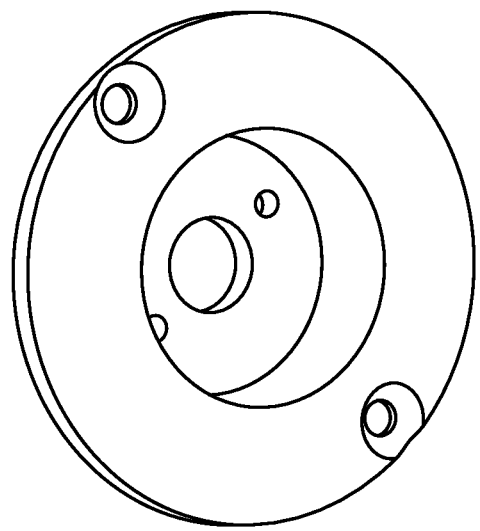
FIG. 24 shows a CAD diagram of an electromagnetic source emitter bracket for the FPTF-ATR spectrometer, according to one embodiment of the present invention.
Figure 25:
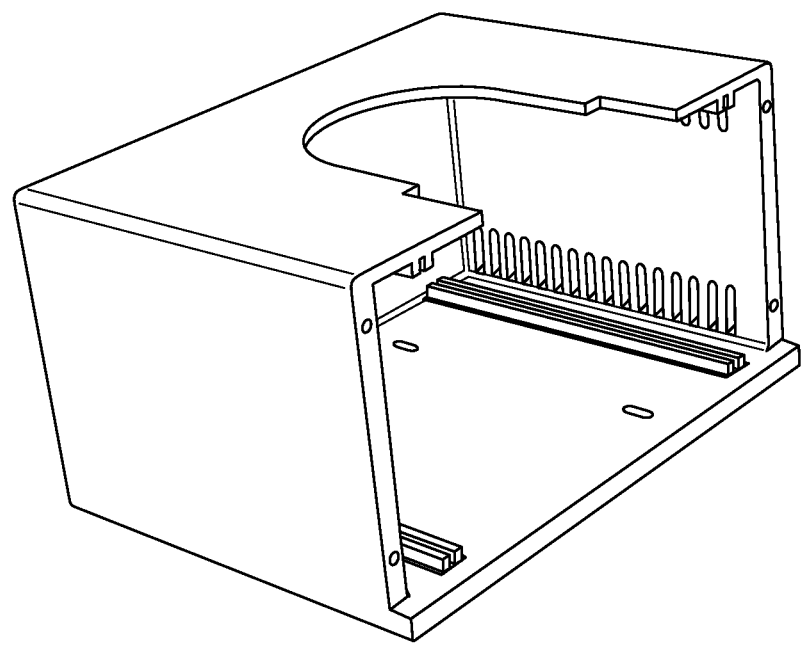
FIG. 25 shows a CAD diagram of an external enclosure for the FPTF-ATR spectrometer, according to one embodiment of the present invention.
Figure 26:
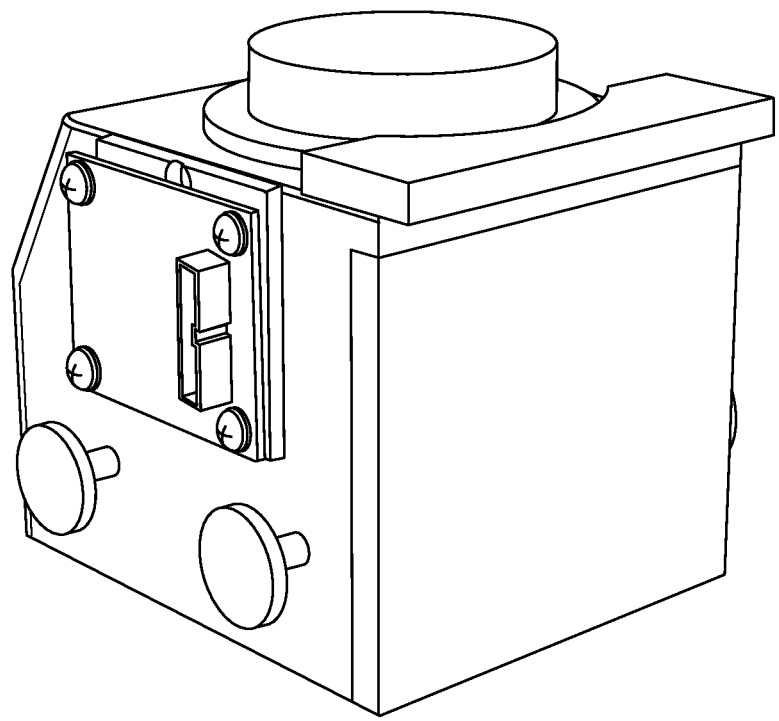
FIG. 26 shows a CAD diagram of a spectrometer module box with emitter and FPTF electronics board of the FPTF-ATR spectrometer, according to one embodiment of the present invention.

FIGS. 23-26 show illustrative CAD diagrams of the component parts of the FPTF-ATR spectrometer, according to just one illustrative embodiment of the present invention. FIG. 23 shows a CAD diagram of a FPTF circuit board mounting bracket for the FPTF-ATR spectrometer, according to one embodiment of the present invention. FIG. 24 shows a CAD diagram of an electromagnetic source emitter bracket for the FPTF-ATR spectrometer, according to one embodiment of the present invention. FIG. 25 shows a CAD diagram of an external enclosure for the FPTF-ATR spectrometer, according to one embodiment of the present invention. Finally, FIG. 26 shows a CAD diagram of a spectrometer module with the emitter and detector of the FPTF-ATR spectrometer mounted, according to one embodiment of the present invention. A rear cover (not shown) is used to close and seal the device.

In conclusion, the inventor developed a non-obvious spectrometer device and mechanism to couple an internal reflection element (IRE) to a FPTF wavelength selector to make a FPRF-ATR spectrometer. The inventor recognized the previously unrecognized opportunity created by coupling a FPTF with an IRE to extend the advantages of the FPTF wavelength selector, which results in a spectrometer that is small, portable, accurate, and easy to use for the analysis of solids and liquids. The reason no one has done this before was the difficulties the inventor has encountered and overcome in the process, as described below.

Firstly, there were difficulties encountered mounting the electromagnetic source and FPTF to achieve the proper optical coupling to the IRE. The source and FPTF have to be held firmly in a very precise location to maximize the amount of light reaching the FPTF. This is needed to obtain the best signal-to-noise ratio spectra possible, increasing sensitivity and accuracy. Special mounting brackets for precisely placing the electromagnetic source and FPTF had to be designed, built, and tested through several iterations, as shown in the FIGS. 23-26.

The second challenge encountered was the design of the transfer optics. Using a flat mirror in the first transfer optics, as was available in off-the-shelf optics modules, did not provide sufficient beam collimation and throughput for optimal results. After performing calculations, design work, and extensive testing, it was found that a parabolic input mirror improved sensitivity and accuracy.

A third challenge was providing a software package and user interface that runs the spectrometer and is easy to use. The only extant software for running the FPTF was difficult to use, geared towards use by electrical engineers, and had no data analysis capability. Additionally, the spectra were not saved to disk in a standard spectroscopy file format. The inventor had to develop custom software that could talk to and control the FPTF, save spectra to disk in a standard spectroscopic format, and have an easy to use graphical user interface that anyone could use.

Lastly, the data analysis was a challenge. For complex samples, such as *cannabis* containing and hops containing materials, the myriad of molecules present means that it is difficult to find an individual peak whose height or area changes due to only changes in the concentration of one analyte. Because of this, a multivariate analysis/chemometrics approach to data analysis was needed. This means measuring spectra of many samples using the FPTF-ATR spectrometer, and then analyzing them by a reference method such as High-Pressure Liquid Chromatography. Then, experimentation with algorithms, data pre-processing, outlier detection, and the number of principal components to include in models was necessary. Lastly, the models had to be validated via the analysis of additional samples.

In summary, difficulties were encountered in mounting the electromagnetic source and FPTF, designing the transfer optics, obtaining a software package that could run the spectrometer and was easy to use, and the complexity of data analysis and model building. The obstacles to building an FPTF-ATR spectrometer would have been overwhelming to one of ordinary skill in the art, which is why it has not been done before. The inventor recognized the opportunity and approach to get around these problems to produce the present invention, as described herein.

One of ordinary skill in the art knows that the use cases, structures, schematics, and flow diagrams may be performed in other orders or combinations, but the inventive concept of the present invention remains without departing from the broader scope of the invention. Every embodiment may be unique, and methods/steps may be either shortened or lengthened, overlapped with other activities, postponed, delayed, and continued after a time gap, such that every user is accommodated to practice the methods of the present invention.

Although the present invention has been described with reference to specific exemplary embodiments, it will be evident that the various modifications and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention as claimed in the appended claims.

REFERENCES

The following references are incorporated by reference in their entireties as if fully set forth herein.

[1] Brian C. Smith, *Fundamentals of Fourier Transform Infrared Spectroscopy*, 2nd Edition. CRC Press, Boca Raton, 2011.
[2] Brian C. Smith, *Infrared Spectral Interpretation: A Systematic Approach*, CRC Press, Boca Raton, 1999.
[3] Brian C. Smith, *Quantitative Spectroscopy: Theory and Practice*, Academic Press, Boston, 2002.
[4] N. J. Harrick, *Internal Reflection Spectroscopy*, Harrick Scientific Corporation, Ossining N.Y., 1987.
[5] Infratec Corp. Application note, *Advanced Features of Infratec Pyroelectric Detectors*.
[6] Michael Starks, *Marijuana Chemistry*, Ronin Publishing, 1977.

[7] Brian C. Smith, *Optimization of Cannabis Grows by Fourier Transform Infrared Spectroscopy*, PerkinElmer Application note, January 2016.

What is claimed is:

1. A chemical analysis device for analyzing sample comprising a solid, said device comprising:
    a source of electromagnetic radiation optically coupled to a first set of transfer optics;
    an internal reflection element optically coupled to said first set of transfer optics, the internal reflection element configured for forming an evanescent wave on at least one sampling surface, said sampling surface configured for being exposed to the sample, said sample interacting with the evanescent wave at the sampling surface;
    a pressure application element configured for applying pressure to said sampling surface or the sample resting upon said sampling surface;
    a second set of transfer optics optically coupled to said internal reflection element;
    a Fabry-Perot tunable filter optically coupled to said second set of transfer optics, said Fabry-Perot tunable filter comprising at least one mobile reflective surface for adjusting bandpass wavelengths;
    a detector element optically coupled to said Fabry-Perot tunable filter that turns electromagnetic radiation into a signal; and
    a communication element to send the signal to a control, display, and data analysis device.

2. The device of claim 1, further comprising:
    a reflective surface moving element for moving the mobile reflective surface of the Fabry-Perot tunable filter.

3. The device of claim 2, wherein the reflective surface moving element is voltage-activated and electrostatically actuated.

4. The device of claim 1, wherein the source of electromagnetic radiation is pulsed.

5. The device of claim 1, wherein the first set of transfer optics comprises a first mirror and a first Zinc Selenide (ZnSe) lens, and the second set of transfer optics comprises a second mirror and a second ZnSe lens.

6. The device of claim 1, wherein the first set of transfer optics comprises a first Zinc Selenide (ZnSe) lens, and the second set of transfer optics comprises a second ZnSe lens.

7. The device of claim 1, wherein the first set of transfer optics comprises a parabolic mirror.

8. The device of claim 1, wherein the internal reflection element comprises a material selected from the group consisting of zinc selenide, silicon, diamond, germanium, and KRS-5.

9. The device of claim 1, wherein the detector element comprises a material selected from the group consisting of deuterated triglycine sulfate, triglycine sulfate, lithium tantalate, mercury cadmium telluride, lead sulfide, silicon, germanium, indium antimonide, indium arsenic antimonide, and indium gallium arsenide.

10. The device of claim 1, wherein the sample is selected from the group consisting of a *cannabis*-containing solid and a *cannabis*-containing solid-liquid mixture.

11. The device of claim 1, wherein the pressure application element is a clamp.

12. The device of claim 1, further comprising: a pressure measurement element for measuring an amount of pressure applied by the pressure application element to the one or more sampling surfaces.

13. The device of claim 1, wherein the pressure application element comprises a slip-clutch element, wherein an amount of pressure applied is limited by the slip-clutch element.

* * * * *